US011154186B2

(12) United States Patent
Sachse et al.

(10) Patent No.: US 11,154,186 B2
(45) Date of Patent: Oct. 26, 2021

(54) DEVICES, SYSTEMS, AND METHODS FOR IMAGING AND TREATING A SELECTED TISSUE

(71) Applicant: UNIVERSITY OF UTAH RESEARCH FOUNDATION, Salt Lake City, UT (US)

(72) Inventors: Frank B. Sachse, Salt Lake City, UT (US); Robert W. Hitchcock, Sandy, UT (US); Nassir F. Marrouche, Park City, UT (US); Nathan J. Knighton, Salt Lake City, UT (US); Chao Huang, Fruit Heights, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 368 days.

(21) Appl. No.: 15/222,858

(22) Filed: Jul. 28, 2016

(65) Prior Publication Data

US 2017/0027503 A1 Feb. 2, 2017

Related U.S. Application Data

(60) Provisional application No. 62/199,585, filed on Jul. 31, 2015.

(51) Int. Cl.
*A61B 1/07* (2006.01)
*A61B 1/00* (2006.01)
(Continued)

(52) U.S. Cl.
CPC .......... *A61B 1/043* (2013.01); *A61B 1/00009* (2013.01); *A61B 1/00154* (2013.01);
(Continued)

(58) Field of Classification Search
CPC . A61B 1/043; A61B 1/00009; A61B 1/00154; A61B 1/0125; A61B 1/015;
(Continued)

(56) References Cited

U.S. PATENT DOCUMENTS 5,429,131 A 7/1995 Scheinman et al.
5,687,737 A 11/1997 Branham et al.
(Continued)

FOREIGN PATENT DOCUMENTS

CN 101453942 A 6/2009
CN 103747756 A 4/2014
(Continued)

OTHER PUBLICATIONS

International Search Report and Written Opinion for PCT/US2016/044845 dated Oct. 7, 2016.
(Continued)

*Primary Examiner* — Timothy J Neal
*Assistant Examiner* — William B Chou
(74) *Attorney, Agent, or Firm* — Workman Nydegger

(57) ABSTRACT

A catheter for imaging and treating a selected tissue and method of use is provided. Imaging, and treatment assemblies may be co-located at a distal end of a single catheter. The imaging assembly may include at least a portion of a confocal microscope. The treatment assembly may include at least a portion of the imaging assembly. A method of treating a selected tissue is also provided. The method may be performed using a single catheter. The imaging and treatment steps of the method may be performed simultaneously.

20 Claims, 26 Drawing Sheets

(51) Int. Cl.
*A61B 1/04* (2006.01)
*A61B 1/018* (2006.01)
*A61B 18/14* (2006.01)
*A61B 1/05* (2006.01)
*A61B 1/015* (2006.01)
*A61B 1/012* (2006.01)
*A61B 18/04* (2006.01)
*A61M 25/00* (2006.01)
*A61B 18/00* (2006.01)
*A61B 5/00* (2006.01)
*A61B 18/02* (2006.01)
*A61B 5/287* (2021.01)

(52) U.S. Cl.
CPC .............. *A61B 1/015* (2013.01); *A61B 1/018* (2013.01); *A61B 1/0125* (2013.01); *A61B 1/05* (2013.01); *A61B 1/07* (2013.01); *A61B 18/04* (2013.01); *A61B 18/1492* (2013.01); *A61M 25/0082* (2013.01); *A61B 5/287* (2021.01); *A61B 5/6852* (2013.01); *A61B 2018/00357* (2013.01); *A61B 2018/00577* (2013.01); *A61B 2018/00791* (2013.01); *A61B 2018/00815* (2013.01); *A61B 2018/00839* (2013.01); *A61B 2018/00982* (2013.01); *A61B 2018/0212* (2013.01)

(58) Field of Classification Search
CPC .. A61B 1/018; A61B 1/05; A61B 1/07; A61B 1/04; A61B 1/06; A61B 1/0676; A61B 18/04; A61B 18/1492; A61B 5/0082; A61B 5/0084; A61B 5/0086; A61B 90/20; A61B 90/25; A61B 90/30; A61M 25/0082; G02B 21/0028; G02B 21/365
USPC .................................................. 600/104, 113
See application file for complete search history.

(56) References Cited

U.S. PATENT DOCUMENTS

| | | | |
|---|---|---|---|
| 6,004,269 A | 12/1999 | Crowley et al. | |
| 6,228,082 B1* | 5/2001 | Baker | A61B 18/1402 606/41 |
| 7,001,383 B2 | 2/2006 | Keidar | |
| 7,499,153 B2 | 3/2009 | Puppels et al. | |
| 8,029,766 B2 | 10/2011 | Elmaleh et al. | |
| 8,106,905 B2 | 1/2012 | Markowitz et al. | |
| 8,316,861 B2 | 11/2012 | Brewer et al. | |
| 8,432,542 B2 | 4/2013 | Marple et al. | |
| 8,496,579 B2* | 7/2013 | Koenig | A61B 1/00172 600/160 |
| 8,876,815 B2 | 11/2014 | Coe et al. | |
| 9,763,642 B2 | 9/2017 | Harks et al. | |
| 10,143,398 B2 | 12/2018 | Altmann et al. | |
| 10,231,706 B2 | 3/2019 | Chen et al. | |
| 2004/0054366 A1* | 3/2004 | Davison | A61B 18/14 606/39 |
| 2004/0092806 A1 | 5/2004 | Sagon et al. | |
| 2004/0092846 A1 | 5/2004 | Watrous | |
| 2004/0153057 A1* | 8/2004 | Davison | A61B 18/1206 606/41 |
| 2005/0033135 A1 | 2/2005 | Govari | |
| 2005/0242298 A1* | 11/2005 | Genet | A61B 5/0068 250/461.2 |
| 2005/0288665 A1* | 12/2005 | Woloszko | A61B 18/1482 606/41 |
| 2006/0041199 A1 | 2/2006 | Elmaleh et al. | |
| 2006/0229515 A1 | 10/2006 | Sharareh et al. | |
| 2006/0253031 A1 | 11/2006 | Altmann et al. | |
| 2007/0038123 A1 | 2/2007 | Fulghum | |
| 2007/0179397 A1 | 8/2007 | Hashimshony et al. | |
| 2007/0299352 A1 | 12/2007 | Harlev et al. | |
| 2008/0183036 A1 | 7/2008 | Saadat et al. | |
| 2008/0306391 A1 | 12/2008 | Hular et al. | |
| 2009/0076375 A1 | 3/2009 | Maschke | |
| 2009/0076498 A1* | 3/2009 | Saadat | A61B 18/1492 606/41 |
| 2009/0231578 A1 | 9/2009 | Ling et al. | |
| 2009/0299195 A1 | 12/2009 | Muller et al. | |
| 2009/0326320 A1 | 12/2009 | Sinofsky et al. | |
| 2011/0028967 A1 | 2/2011 | Rollins et al. | |
| 2011/0082451 A1 | 4/2011 | Melsky | |
| 2011/0118590 A1 | 5/2011 | Zhang | |
| 2011/0301438 A1 | 12/2011 | Sachse et al. | |
| 2012/0053452 A1 | 3/2012 | Tal | |
| 2012/0108957 A1 | 5/2012 | Desai | |
| 2012/0172724 A1 | 7/2012 | Hill et al. | |
| 2012/0281218 A1* | 11/2012 | Schnitzer | A61B 1/043 356/432 |
| 2012/0302892 A1 | 11/2012 | Lue et al. | |
| 2013/0102862 A1 | 4/2013 | Mercader et al. | |
| 2013/0218019 A1 | 8/2013 | Abraham | |
| 2014/0018792 A1 | 1/2014 | Gang et al. | |
| 2014/0031802 A1 | 1/2014 | Melsky et al. | |
| 2014/0058246 A1 | 2/2014 | Boveja et al. | |
| 2014/0081113 A1 | 3/2014 | Cohen et al. | |
| 2014/0088418 A1 | 3/2014 | Radulescu et al. | |
| 2014/0171942 A1 | 6/2014 | Werneth et al. | |
| 2015/0011843 A1* | 1/2015 | Toth | A61N 1/36185 600/301 |
| 2015/0119708 A1 | 4/2015 | Sachse et al. | |
| 2015/0182282 A1* | 7/2015 | Zemel | A61B 18/1492 606/41 |
| 2015/0351722 A1 | 12/2015 | Chen et al. | |
| 2018/0103852 A1* | 4/2018 | Dagdeviren | G16H 20/17 |
| 2020/0022573 A1 | 1/2020 | Sachse et al. | |

FOREIGN PATENT DOCUMENTS

| | | |
|---|---|---|
| CN | 105163651 A | 12/2015 |
| WO | 2006020920 | 2/2006 |
| WO | 2007146864 | 12/2007 |
| WO | 2014028584 | 2/2014 |
| WO | 2014165990 | 10/2014 |
| WO | 2015073932 | 5/2015 |

OTHER PUBLICATIONS

International Search Report and Written Opinion for PCT/US2018/016314 dated Mar. 28, 2018.
Diaz et al., "Spectral classifier design with ensemble classifiers and misclassification-rejection: application to elastic-scattering spectroscopy for detection of colonic neoplasia", Journal of biomedical optics., 16.6 (2011), 067009.
Femnou et al., "Intra-cardiac Side-Firing Light Catheter for Monitoring Cellular Metabolism using Transmural Absorbance Spectroscopy of Perfused Mammalian Hearts", JoVE (Journal of Visualized Experiments), 147 (2019):e58992.
Knighton et al., "Towards Cardiac Tissue Characterization Using Machine Learning and Light-Scattering Spectroscopy," USA, 84112, 2015, 26 pages.
Knighton et al., "Towards Intraoperative Quantification of Atrial Fibrosis Using Light Scattering Spectroscopy and Convolutional Neural Networks," UT 84112, USA, 16 pages.
Rajitha et al., "Machine learning classification of human joint tissue from diffuse reflectance spectroscopy data", Biomedical optics express, 10.8 (2019): 3889-3898.
Final Office Action received for U.S. Appl. No. 15/222,858, dated Nov. 15, 2019.
International Search Report and Written Opinion issued in PCT/US2018/016314 dated Mar. 2, 2018.
Office Action received for U.S. Appl. No. 15/222,858, dated Jan. 23, 2020.
Office Action received for U.S. Appl. No. 15/222,858, dated Feb. 28, 2019.
International Search Report and Written Opinion received for PCT Patent Application No. PCT/US2020/065648, dated May 7, 2021, 12 pages.

(56) References Cited

OTHER PUBLICATIONS

Non-Final Office Action received for U.S. Appl. No. 16/482,389, dated Aug. 17, 2021, 21 pages.

* cited by examiner

DEVICES, SYSTEMS, AND METHODS FOR IMAGING AND TREATING A SELECTED TISSUE

CROSS-REFERENCE TO RELATED APPLICATIONS

This application claims priority to and benefit of U.S. Provisional Patent Application No. 62/199,585, filed Jul. 31, 2015, the entire contents of which are incorporated by reference herein.

BACKGROUND

Atrial fibrosis is an important predictor of the success of treatment (e.g., ablation and/or drug delivery) for therapy of atrial fibrillation. Methods of delayed enhancement magnetic resonance imaging and image processing have been developed to characterize the degree of pre-treatment fibrosis in arrhythmia patients. However, there is no existing method for non-invasive, or even minimally invasive staged characterization of atrial fibrosis at a microscopic scale.

What is needed in the art are devices, systems, and methods that perform staged characterization of tissue at a microscopic scale. There is a further need in the art for devices, systems, and methods of performing minimally invasive characterization of tissue before, during, and after therapeutic interventions. There is still a further need in the art for devices, systems, and methods of integrating real-time tissue imaging with computational imaging processing, electrical measurements, and treatment.

SUMMARY

In one embodiment, a device for imaging and treating a selected tissue of a subject is described. The device includes a sheath having a longitudinal axis, an inner surface, and a distal tip. The inner surface of the sheath defines a bore. An imaging assembly is configured to produce one or more images of the selected tissue of the subject. A treatment assembly is configured to treat the selected tissue of the subject.

In some embodiments, the images are microscopic images. The device, in some embodiments, may include a mapping assembly configured to record electrical activity within the selected tissue of the subject. In some embodiments, the treatment assembly includes one or more of an energy application assembly configured to apply energy to the selected tissue of the subject and a drug delivery assembly configured to deliver an agent to the selected tissue.

A distal end of the imaging assembly and a distal end of the treatment assembly, in some embodiments, are disposed at the distal tip of the sheath. In some embodiments, the sheath is steerable. An outer diameter of the sheath, in some embodiments, is less than 5 mm.

In some embodiments, the imaging assembly comprises at least a portion of a confocal microscope assembly. The distal tip of the sheath, in some embodiments, defines a port in communication with the bore of the sheath.

In some embodiments, one or more of at least a portion of the imaging assembly, at least a portion of the energy application assembly, and at least a portion of the mapping assembly are configured for advancement through the port independently. The device may include at least one conduit positioned within the bore of the sheath and positioned in communication with the port. At least one of the portion of the imaging assembly, the portion of the energy application assembly, and at least the portion of the mapping assembly, in some embodiments, are configured for selective advancement within the at least one conduit and through the port. In some embodiments, the at least one conduit includes a base conduit positioned in communication with the port and at least one of a first branch conduit in communication with the base conduit, the first branch conduit configured to receive and permit selective advancement and retraction of at least the portion of the imaging assembly, a second branch conduit in communication with the base conduit, the second branch conduit configured to receive and permit selective advancement and retraction of at least the portion of the energy application assembly, and a third branch conduit in communication with the base conduit, the third branch conduit configured to receive and permit selective advancement and retraction of at least the portion of the mapping assembly. The base conduit and each of the first, second, and third branch conduits of the at least one conduit, in some embodiments, cooperate to define Y-shaped conduit assemblies.

The imaging assembly, in some embodiments, includes a fiber-optic bundle configured for communication with at least one of a light source and a light detector. In some embodiments, the fiber-optic bundle has a diameter of less than about 3 mm. The fiber-optic bundle, in some embodiments, is configured to produce an image of the selected tissue of the subject at a resolution of less than about 4 µm.

In some embodiments, the imaging assembly includes a conductive housing. The conductive housing of the imaging assembly, in some embodiments, includes at least a portion of the energy application assembly. In some embodiments, the conductive housing of the imaging assembly includes at least a portion of the mapping assembly. The imaging assembly, in some embodiments, includes at least one objective lens positioned proximate the distal tip of the sheath and within the conductive housing.

The mapping assembly, in some embodiments, includes a plurality of mapping electrodes. In some embodiments, each mapping electrode of the plurality of mapping electrodes of the mapping assembly is configured to record electrical activity within the selected tissue of the subject. The mapping electrodes of the mapping assembly, in some embodiments, are circumferentially spaced about the distal tip of the sheath. In some embodiments, the plurality of mapping electrodes of the mapping assembly include at least four electrodes.

In some embodiments, the energy application assembly includes at least one energy application zone configured to selectively apply energy to the selected tissue of the subject to thereby ablate the selected tissue. The at least one energy application zone, in some embodiments, is configured to apply radiofrequency energy to the selected tissue of the subject. In some embodiments, the at least one energy application zone includes at least one ablation electrode. Each ablation electrode of the energy application assembly, in some embodiments, has an outer diameter ranging from about 1 mm to about 4 mm.

In one embodiment, a method for treating a selected tissue of a subject is disclosed. The method includes inserting a catheter into the subject so that a distal tip of the catheter is in communication with the selected tissue. The catheter includes a sheath having an inner surface defining a bore. Without withdrawing the catheter, one or more images of the selected tissue is produced. Without withdrawing the catheter, an operation of a treatment assembly is controlled based at least in part upon the first and/or second outputs. Without withdrawing the catheter, portions of the selected tissue is treated using the treatment assembly. The selected tissue is imaged at least one of before, during, and after the application of energy.

In some embodiments, the method further includes without withdrawing the catheter, mapping electrical signals of the selected tissue. The one or more images, in some embodiments, are a first output and wherein the mapped electrical signals are a second output. In some embodiments, controlling an operation of a treatment assembly is based at least in part upon the first and/or second outputs. The treatment assembly, in some embodiments, is an energy application assembly. In some embodiments, the treatment assembly is a drug delivery assembly.

The imaging and treatment, in some embodiments, are performed while the catheter remains in the subject. In some embodiments, the subject is a blood-filled heart. The subject, in some embodiments, is a beating heart. In some embodiments, the selected tissue is adjacent to the interior surface (endocardium) of a heart.

In some embodiments, imaging the selected tissue and treating the selected tissue are performed simultaneously. The imaging of the selected tissue, in some embodiments, is performed using at least a portion of the treatment assembly. In some embodiments, the mapping of the selected tissue is performed using at least a portion of the treatment assembly.

Producing an image of the selected tissue, in some embodiments, includes illuminating the selected tissue and/or exciting fluorophores within the selected tissue with light and receiving emitted light from the selected tissue using an imaging assembly. In some embodiments, each of the imaging, mapping, and treatment assemblies is selectively advanced through the distal tip of the catheter, thereby extending beyond the distal tip of the catheter, when performing the imaging, mapping, and treatment steps, respectively.

In some embodiments, inserting the catheter into the subject so the distal tip of the catheter is in communication with the selected tissue further includes inserting the catheter so that the distal tip of the catheter is in communication with the selected tissue, steering at least the distal tip of the catheter to be adjacent to the selected tissue, or steering at least a distal portion of the imaging, mapping, and/or ablation assemblies to be adjacent to the selected tissue.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIGS. 2-1 through 2-3 illustrate embodiments of devices for imaging and treating tissue;

FIG. 3-1 through 3-3 illustrates an embodiment of a device for imaging and treating tissue with a port, a base conduit, and branch conduits;

FIGS. 5-1 and 5-2 illustrate another embodiment of a steerable device for imaging and treating tissue;

FIGS. 6-1 and 6-2 illustrate a distal end of an embodiment of an imaging assembly;

FIGS. 12-1 and 12-2 illustrate embodiments of a catheter for imaging and treating tissue with multiple mapping electrodes;

FIGS. 13-1 and 13-2 illustrate another embodiment of a catheter for imaging and treating tissue with multiple mapping electrodes;

FIGS. 14-1 and 14-2 illustrate an embodiment of a catheter for imaging and treating tissue where imaging, mapping, and treatment assemblies are co-located at a distal end of the catheter;

FIG. 15-1 illustrates a flowchart of a method of treating a selected tissue;

FIG. 15-2 illustrates a flowchart of a method 1500 of treating a selected tissue;

FIGS. 18-1 and 18-2 illustrate an embodiment of a catheter 1800 performing an imaging step of the method for treating a selected tissue;

FIGS. 25-1, 25-2, and 25-3 illustrate cross-sectional views of a tissue that has been treated (e.g., ablated);

FIGS. 27-1 and 27-2 illustrate an embodiment of a catheter for imaging and treating tissue in a beating heart.

DETAILED DESCRIPTION

The present disclosure includes devices, systems, and methods for imaging, treating, and/or mapping a selected tissue of a subject. The device, which is often referred to in a non-limiting fashion as a catheter, includes an imaging assembly, a treatment assembly, and a mapping assembly. A treatment assembly may include an energy application assembly and/or a drug delivery assembly. At least a portion of each of these assemblies may be co-located at the distal end or tip of the catheter so that only one catheter is needed to perform the imaging, mapping, and treating of a selected tissue of a subject, such as, for example, the interior tissue of a heart. At least one embodiment described herein enables the imaging, mapping, and treatment (e.g., ablation and/or drug delivery) of a selected tissue to be performed with a single instrument without the need to insert multiple instruments into a subject. In other words, the imaging, mapping, and treatment (e.g., ablation and/or drug delivery) may be performed without inserting an additional imaging, mapping, or treatment (e.g., ablation and/or drug delivery) device.

At least one or more embodiments disclosed herein may provide the following advantages: The integration of steering, imaging, mapping and treatment (e.g., ablation and/or drug delivery) in a single device will allow an operator, such as a doctor, to develop and evaluate new diagnostic and therapeutic approaches. One example application is cardiac ablation using the energy application assembly guided by images of tissue microstructure from the imaging assembly. Another example application is diagnosis of diseases based on integrated imaging of tissue microstructure and electrical mapping.

At least one embodiment described herein is capable of treating (e.g., ablation and/or drug delivery) internal heart tissue while the heart is blood filled and beating. For example, at least one embodiment described herein may image, map, and treat (e.g., ablate and or deliver drug) a portion of an interior surface of the heart tissue with a single device while the heart is filled with blood and/or beating.

Figure 1:
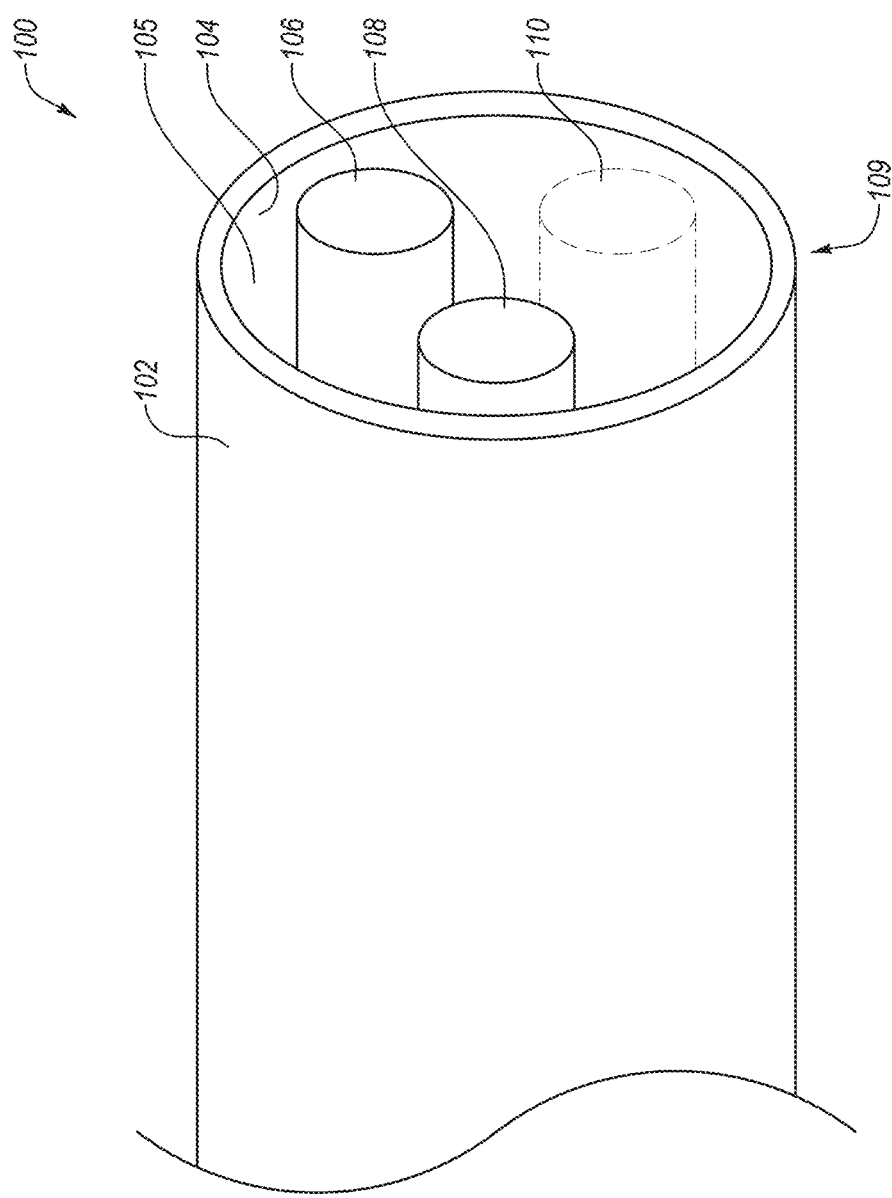
FIG. 1 illustrates an embodiment of a device for imaging and treating tissue.

FIG. 1 illustrates an embodiment of a device (e.g., a catheter 100) for imaging, treating (e.g., ablating and/or delivery drug), and optionally mapping tissue. The catheter 100 includes an outer sheath 102 and an inner surface 104. The inner surface 104 of the outer sheath 102 defines a bore 105. The outer sheath 102 may be made of any suitable, biocompatible material. These materials may include, but are not limited to, typical thermoplastic polymers used in catheter extrusion and construction, typical thermoset polymers used in catheter extrusion and construction and composite combinations of these types of materials to imbue the catheter with specific physical, electrical, optical and mechanical properties. Examples of thermoplastic materials that may be used include, but are not limited to, polyurethane, nylon, fluoropolymers, pebax, polyethylene, polypropylene, vinyls and copolymers of these types of materials.

Examples of thermoset materials may be used include but are not limited to: polyimide, epoxy, silicone and copolymers of these types of materials. Other materials such as metals and polymer filaments may be used in the construction of these catheters to impart specific physical, electrical, optical and mechanical properties.

An imaging assembly 106 and an energy application assembly 108, as well as an optional mapping assembly 110 (shown in phantom), are each shown at least partially disposed within the bore 105 at the distal tip 109 of the catheter 100. At least part of the imaging assembly 106, the energy application assembly 108, and the mapping assembly 110 may be co-located at the distal tip 109 of the catheter 100. For example, a distal end of the imaging assembly 106, a distal end of the energy application assembly 108, and a distal end of the mapping assembly 110 may be located at the distal tip 109.

Although the various embodiments disclosed herein are generally directed to energy application assemblies, in some embodiments in addition to or instead of the energy application assembly a drug delivery assembly may be used. The drug delivery assembly may include a lumen through which various agents may be delivered. The agents that may be delivered may include, but are not limited to, beneficial agents such as cytotoxins, antifibrotic drugs, anti-inflammatory drugs, ion channels blockers and activators, cytokines, other drugs, or combinations thereof and/or tissue ablating agents, such as alcohol.

The integration of the imaging assembly 106, the energy application assembly 108, and the mapping assembly 110 facilitates, in at least one embodiment, the imaging, treatment (e.g., ablation and/or drug delivery), and/or mapping of a selected tissue to be performed with a single instrument, such as the catheter 100 illustrated in FIG. 1, without the need to insert multiple instruments into a subject.

At least one embodiment of a device (e.g., catheter 100) may facilitate the imaging, treating (e.g., ablating and/or delivering drug), and/or mapping of a selected tissue to be performed from the inside of the subject, without the need for additional imaging or mapping instruments. For example, in at least one embodiment, it is not necessary to use a computer tomographic system, magnetic resonance imaging system, or fluoroscope exterior to the subject in order to image the selected tissue during a treatment (e.g., ablation and/or delivering drug) and mapping of the selected tissue. In at least one embodiment with a mapping assembly (e.g., mapping assembly 110), it may not be necessary to use additional mapping instruments to map the electrical activity of the selected tissue while a separate instrument (e.g., catheter 100) images and/or treats (e.g., ablates and/or delivering drug) the selected tissue from inside the subject. Components of the other devices (e.g., catheters) described herein may be incorporated into, and vice versa, the catheter 100 of FIG. 1.

Figures 1, 2:
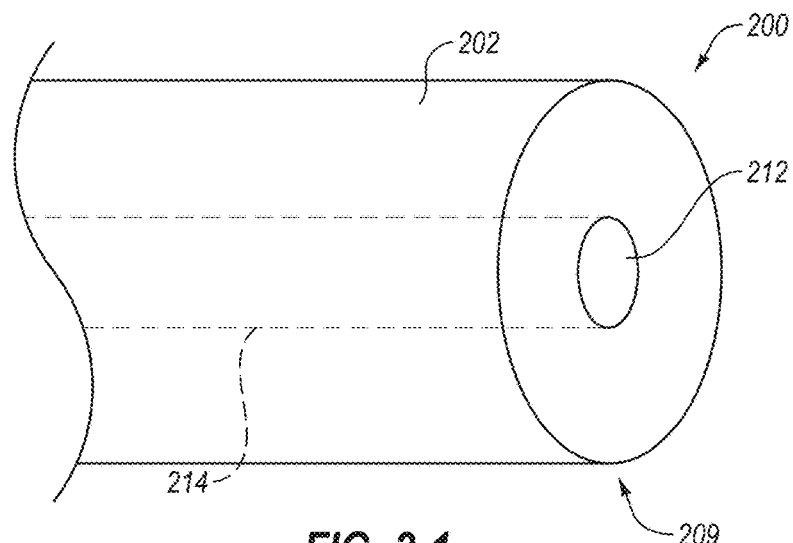
Figure 2:
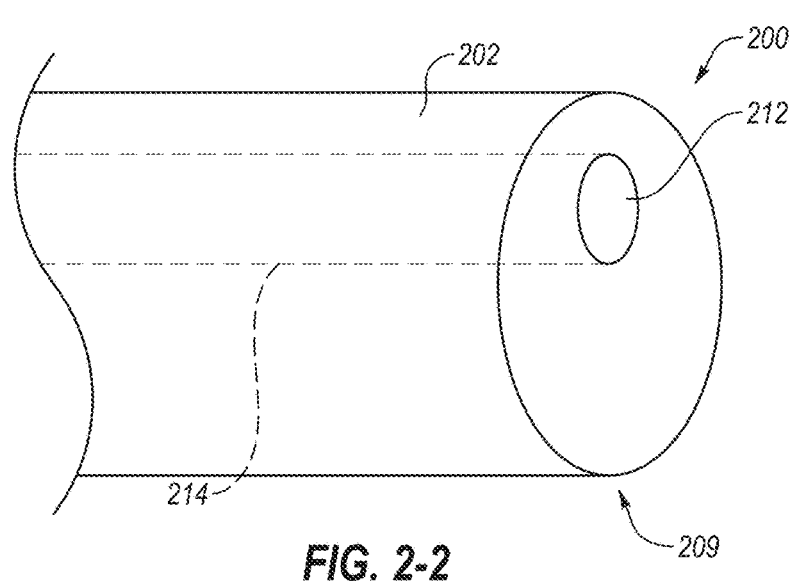
Figures 2, 3:
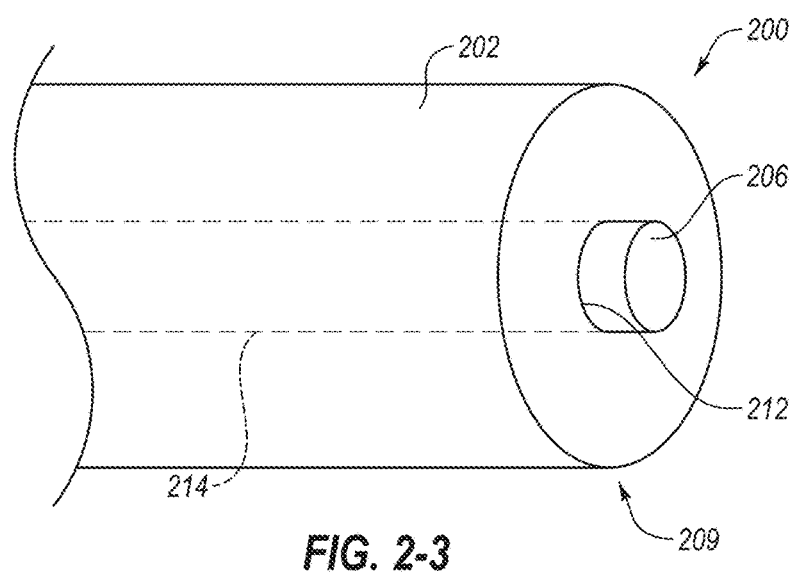
Figures 1, 3:
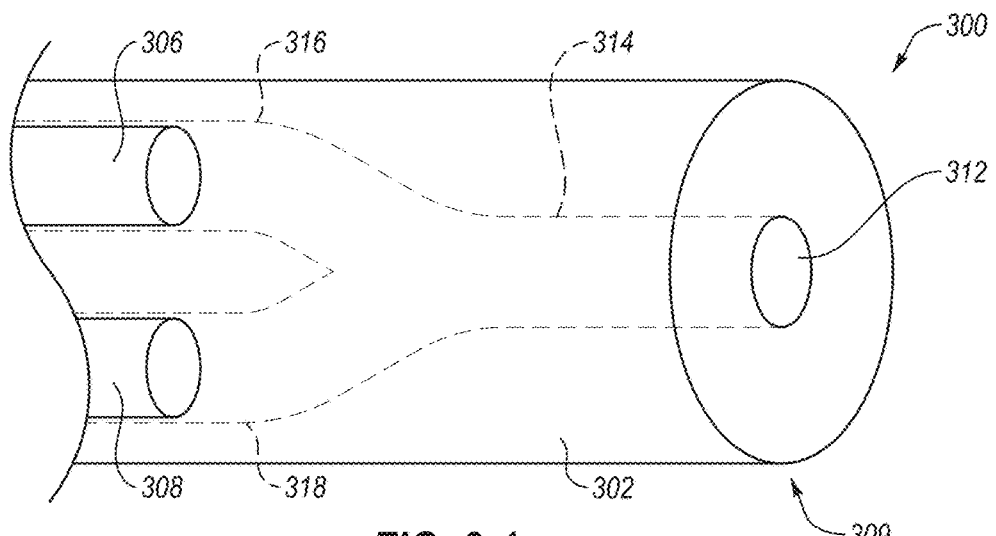
Figures 2, 3:
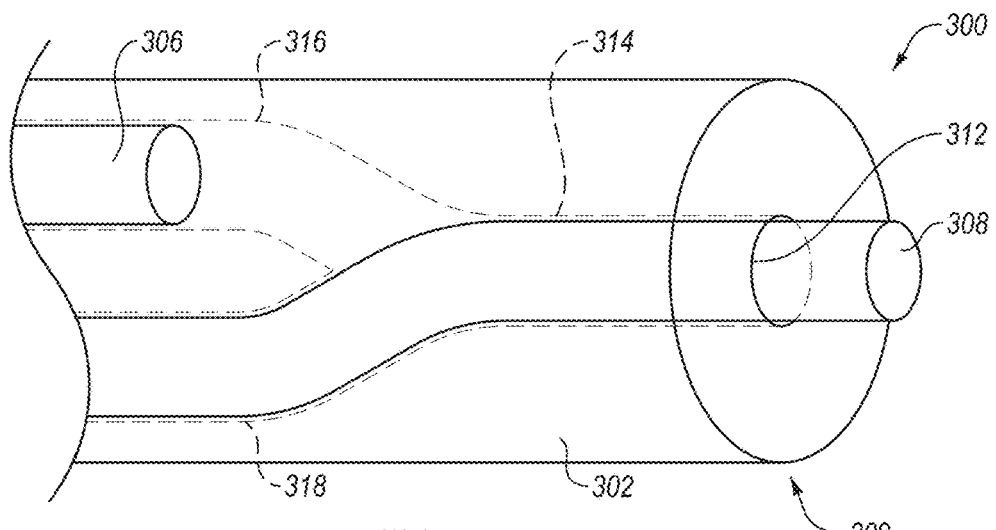
Figure 3:
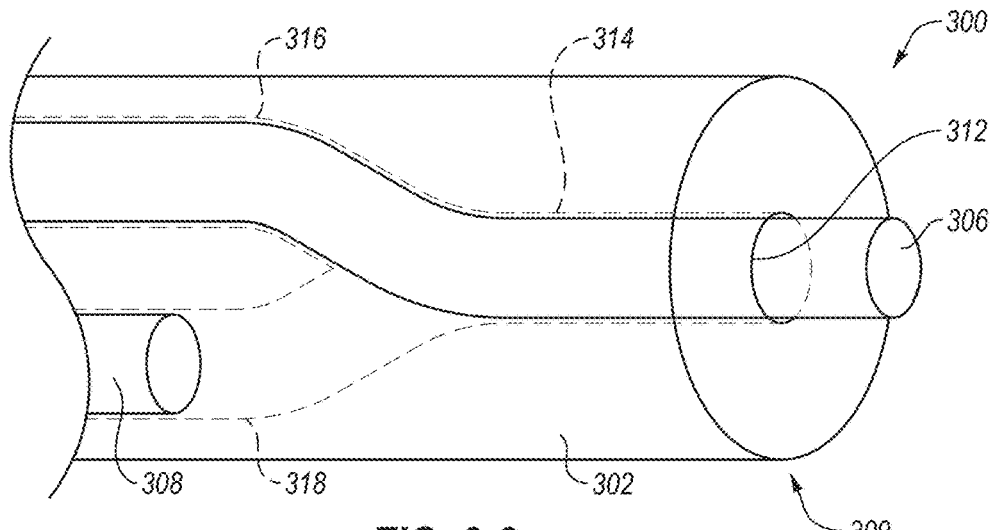

FIGS. 2-1 through 2-3 illustrate embodiments of a device (e.g., catheter 200) for treating tissue. The catheter 200 may include a sheath 202. The catheter 200 includes a port 212. The port 212 may be centrally located (e.g., coaxial with a longitudinal axis of the catheter 200) on a distal tip 209 of the catheter 200, as shown in FIG. 2-1, or it may not be centrally located (e.g., offset from and/or nonparallel with the longitudinal axis) on the distal tip 209, as shown in FIG. 2-2.

A conduit 214 may be in communication with the port 212 and extend into the catheter 200. As illustrated in FIG. 2-3, the conduit 214 and port 212 may provide a pathway for an assembly, such as an imaging assembly 206 (or an energy application assembly 108, mapping assembly 110, other assemblies, or combinations thereof), residing within the catheter 200, to advance through the port 212 beyond the distal tip 209 of the catheter 200. In other words, one or more assemblies (e.g., imaging assembly 206, energy application assembly 108, or mapping assembly 110) may be selectively advanceable within the conduit 214. Other embodiments of a catheter may include multiple ports and multiple conduits. Components of the other devices (e.g., catheters) described herein may be incorporated into, and vice versa, the catheter 200 of FIGS. 2-1 through 2-3.

FIG. 3-1 through 3-3 illustrates an embodiment of a catheter 300 with a port 312, a base conduit 314, and branch conduits 316, 318. The catheter 300 may include a sheath 302. The catheter 300 includes multiple branch conduits. FIGS. 3-1 through 3-3 illustrate two assemblies 306, 308 that may reside within the branch conduits 316, 318, as best seen in FIG. 3-1. Although the catheter 300 is shown with two branch conduits 316, 318, more or fewer branch conduits may be used. As shown, two of the branch conduits may form a Y-shape.

Each branch conduit 316, 318 may be in communication with the base conduit 314. One or more assemblies (e.g., imaging assembly 106, an energy application assembly 108, a mapping assembly 110, imaging assembly 206, assembly 306, assembly 308, other assemblies, or combinations thereof) residing in two or more branch conduits (e.g., one or more branch conduits 316, 318) may be selectively advanced into the branch conduits. For example, a first assembly (e.g., one of the assemblies described herein) may be advanced and/or retracted into, through, out of the base conduit 314, or combinations thereof and a second assembly may be advanced and/or retracted into, through, out of the base conduit 314 or combinations thereof.

In some embodiments, each assembly may selectively extend beyond the distal tip 309 of the catheter 300 as illustrated in FIGS. 3-1 and 3-2. In other embodiments, the assemblies 306, 308 may not necessarily be advanced beyond the distal tip 309 of the catheter 300. For example, an assembly 306, 308 may be advanced so it is flush with the distal tip 309 of the catheter 300 and not extending beyond the port 312. In another example, an assembly (e.g., one of the assemblies described herein) may be advanced so that it resides in the base conduit 314 but remains within the catheter 300.

Components of the other devices (e.g., catheters) described herein may be incorporated into, and vice versa, the catheter 300 of FIGS. 3-1 through 3-3. For example, other embodiments described herein may have one or more assemblies that are selectively advanceable through a base conduit.

Figure 4:
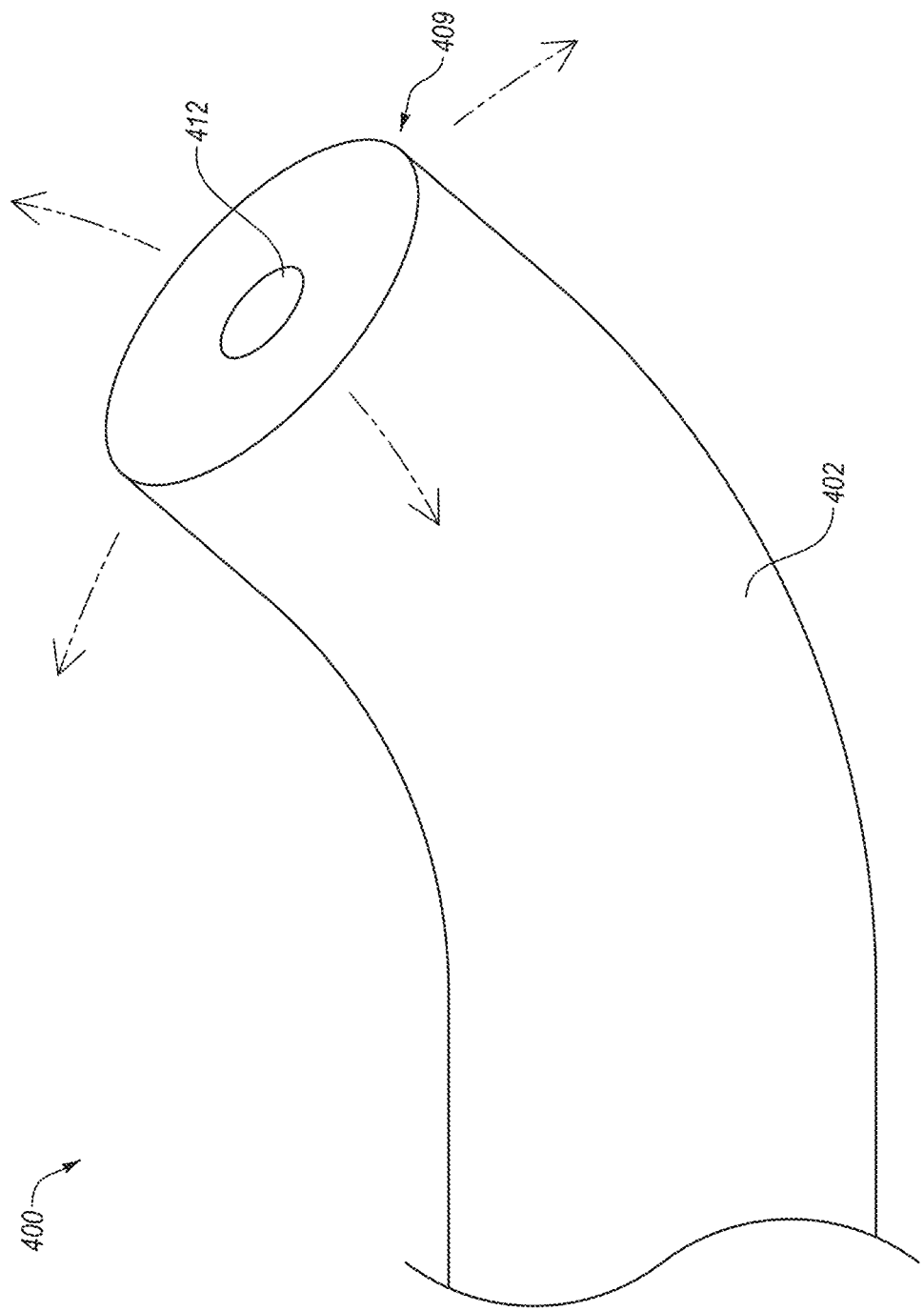
FIG. 4 illustrates an embodiment of a steerable device for imaging and treating tissue.

FIG. 4 illustrates an embodiment of a catheter 400 that is steerable. The catheter 400 may include a sheath 402, port 412, other components described herein, or combinations thereof. The distal tip 409 of the catheter 400 may be manipulated and/or bent by an operator, such as a doctor. The catheter 400 is shown as being bent or steered at the distal tip 409 of the catheter 400 but may also be steerable at other portions of the catheter. For example, the catheter 400 may be bent and/or steered closer to a proximal portion (not shown) of the catheter 400 or a middle portion (not shown) of the catheter 400. The catheter 400 may be steered in any direction and bent at various angles. In some embodiments, the catheters described herein may be steered by a steerable guide catheter and/or may steered as described herein.

Components of the other devices (e.g., catheters) described herein may be incorporated into, and vice versa, the catheter 400 of FIG. 4. For example, other embodiments described herein may be steerable.

Figures 1, 5:
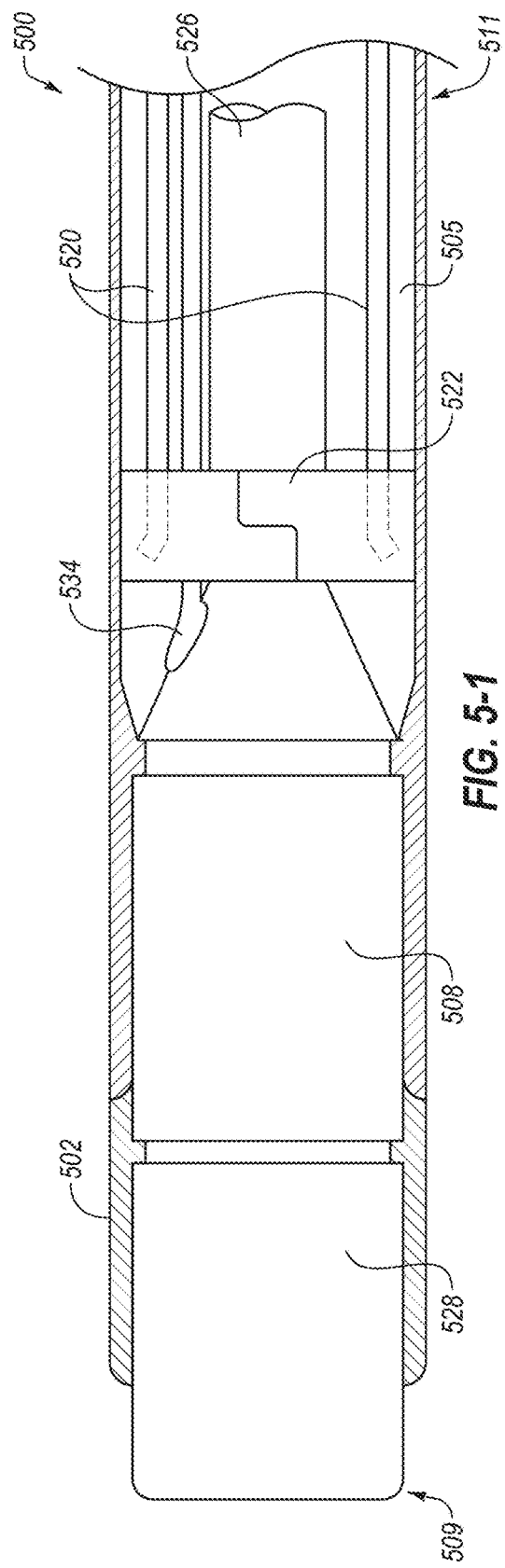
Figures 2, 5:
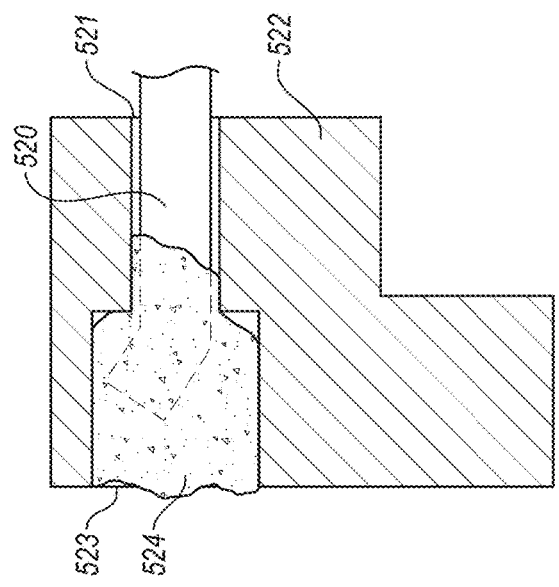

FIGS. 5-1 and 5-2 illustrate an embodiment of a steerable catheter 500. The catheter 500 may include a sheath 502. Actuation wires 520 may be disposed within the bore 505 and run longitudinally from a proximal end 511 of the catheter 500 to a distal tip 509 of the catheter 500. The actuation wires 520 may be secured to an attachment collar 522. The attachment collar 522 may be secured to the sheath 502 of the catheter 500. When an actuation wire 520 is pulled toward a proximal end 511 of the catheter 500, the catheter 500 may tend to curl or bend toward a side of the catheter 500 where the actuation wire 520 is secured to the attachment collar 522. Each actuation wire 520 may be pulled.

FIG. 5-2 illustrates a section of an embodiment of an attachment collar 522, to which an actuation wire 520 has been secured. The actuation wire 520 may be inserted through an attachment collar bore 521 and into an attachment collar cavity 523. The portion of the actuation wire 520 that is inside the cavity 523 may be bent, crimped, or melted so that it cannot be easily pulled out of the cavity 523 and bore 521. Additionally, an epoxy 524 or weld material may be added to the attachment collar cavity 523 in order to further secure the actuation wire 520 to the attachment collar 522. Examples of epoxies and/or weld materials that may be used include, but are not limited to, one and two part epoxies (e.g., EPO-TEK 301, Masterbond, Loctite), light-cure adhesives (e.g., Loctite 3311, Dymax 987, and others), urethane acrylates, polyurethanes and polysulfides. In certain embodiments a metal weld may be used in which a laser beam melts and joins the two metal structures.

FIG. 5-1 illustrates an embodiment of a catheter 500 that includes two actuation wires 520. Other embodiments may include one actuation wire 520 or three or more actuation wires 520. Each actuation wire 520 may facilitate movement of the distal tip 509 of the catheter 500 in one direction. For example, the actuation wires 520 may move the catheter 500 near the attachment collar 522. Therefore, increasing the number of actuation wires 520 connected to the attachment collar 522 may increase the number of directions in which the catheter may be bent and/or steered.

Furthermore, multiple attachment collars 522 may be attached to the catheter 500 along its length. Multiple attachment collars 522 may enable multiple sections of the catheter 500 to be bent and/or steered. For example, the attachment collar 522 shown in FIG. 5-1 is located near the distal tip 509 of the catheter 500, enabling the distal tip 509 to be bent and/or steered. Another attachment collar may be added to a more proximal portion (not shown) of the catheter 500, allowing the more proximal portion of the catheter 500 to be bent and/or steered. The location of the one or more attachment collars 522 may determine where the catheter may be bent and/or steered.

The energy application assembly 508 may be connected to an energy application wire 534 as shown. The energy application assembly 508 will be described further detail below. The imaging assembly 506 may be positioned within an imaging housing 528. The imaging housing 528 will be described in further detail below. The imaging housing 528 may include a fiber-optic bundle 526. The fiber-optic bundle 526 may be used to facilitate imaging of the selected tissue, as further described below.

Components of other devices (e.g., for imaging, treating (e.g., ablating and/or delivering drug), and/or mapping) may be incorporated into, and vice versa, the catheter 500 of FIGS. 5-1 through 5-3. For example, other embodiments described herein may include actuation wires 520 and/or attachment collars 522.

Figures 1, 6:
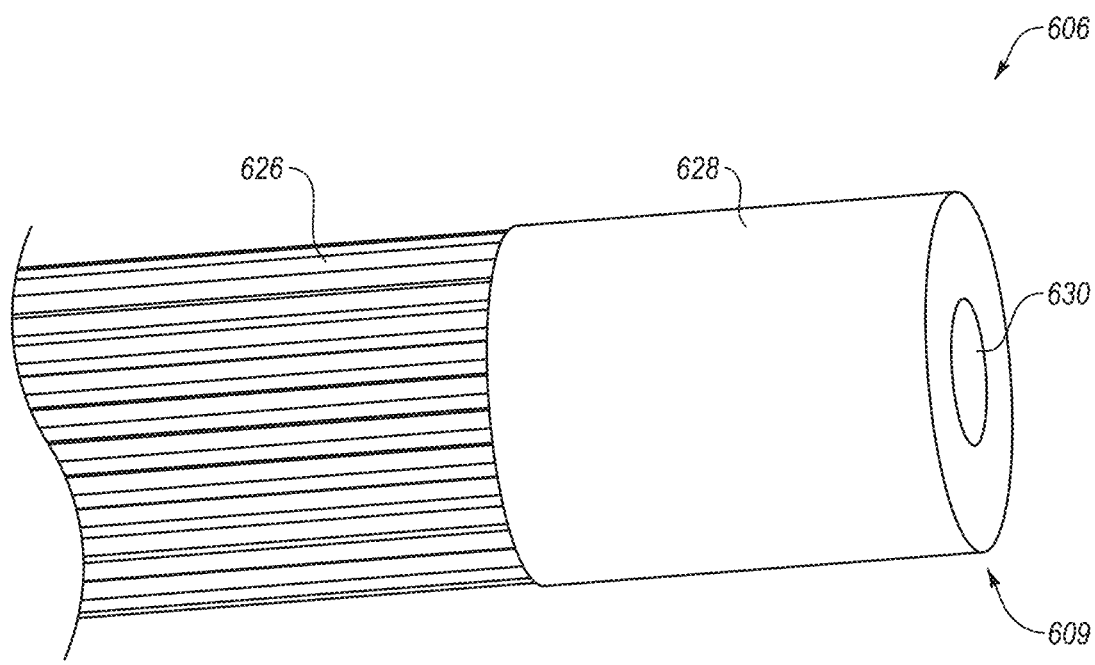
Figures 2, 6:
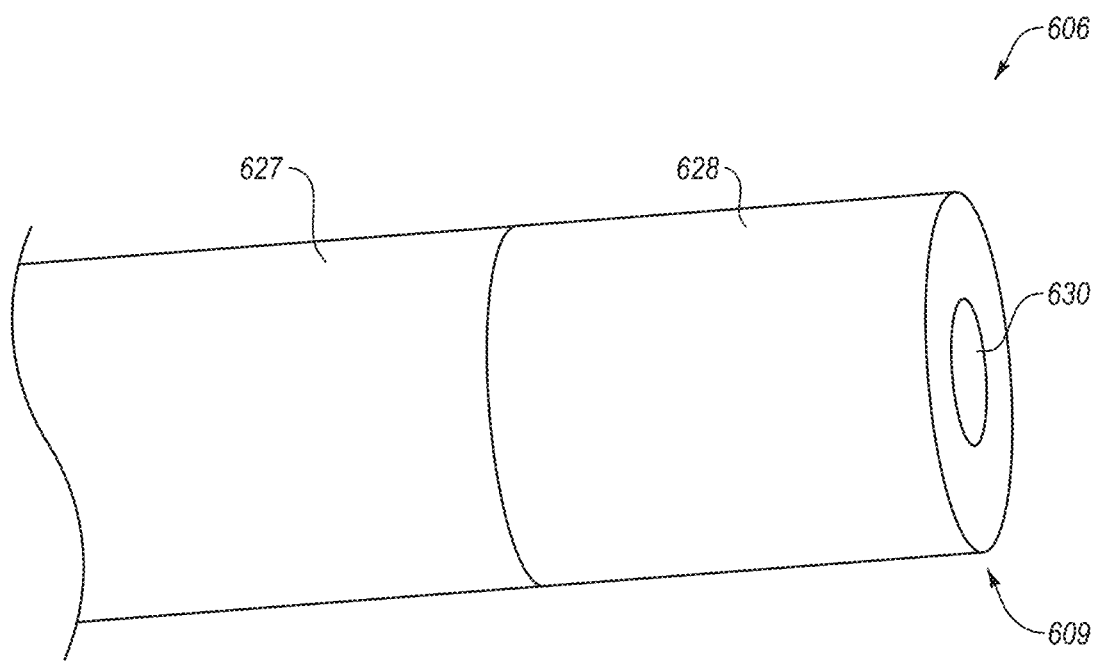

FIGS. 6-1 and 6-2 illustrate a distal end 609 of an embodiment of an imaging assembly 606 that may include a fiber-optic bundle 626, an imaging housing 628, and an aperture 630. As used herein, the term "fiber-optic bundle" is understood to refer to one or more optical fibers that individually and/or collectively transmit light as further disclosed herein.

FIG. 6-2 illustrates an embodiment that includes a fiber-optic bundle sheath 627 covering the fiber-optic bundle 626. As shown in FIG. 6-1, the fiber-optic bundle 626 may be in communication with the imaging housing 628. The imaging housing 628 may have an aperture 630 at the distal end 609 through which light may be transmitted out of and/or received into the imaging assembly 606.

Components of the other devices (e.g., for imaging and treating (e.g., ablating and/or delivering drug)) described herein may be incorporated into, and vice versa, the catheter 600 of FIGS. 6-1 and 6-2. For example, other embodiments described herein may include one or more components of the imaging assembly 606.

Figure 7:
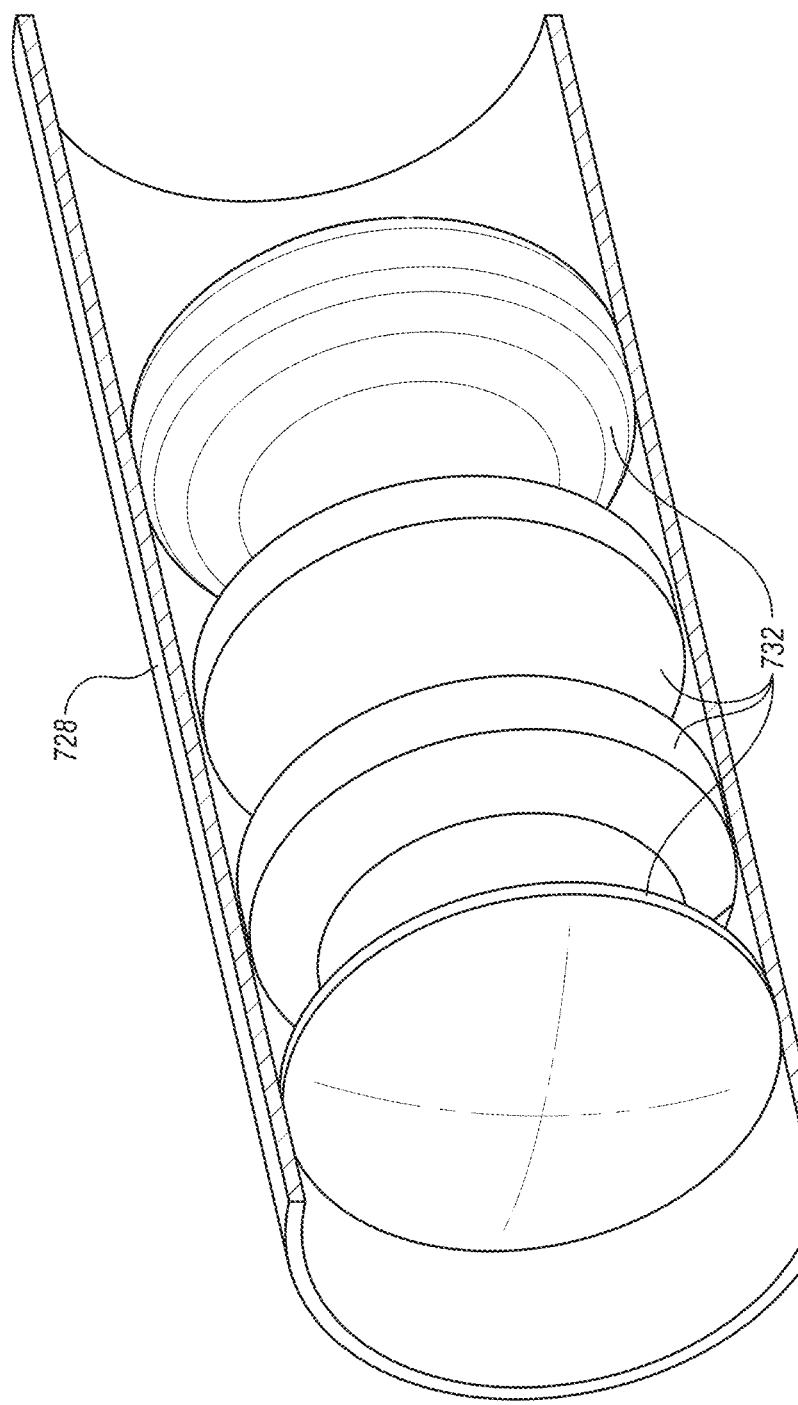
FIG. 7 illustrates an embodiment of an imaging housing.

FIG. 7 illustrates an embodiment of at least one lens 732 that resides inside an imaging housing 728. The at least one lens 732 may be configured such that light transferred through a fiber-optic bundle (e.g., fiber-optic bundle 626) may be focused at a desired area and/or point on and/or within a selected tissue. The lenses 732 may be configured to receive light emitted from the selected tissue back into a fiber-optic bundle. The lenses 732 may have a common longitudinal axis that is parallel to a longitudinal axis of the imaging housing 728.

Components of the other devices (e.g., for imaging and treating (e.g., ablating and/or delivering drug)) described herein may be incorporated into, and vice versa, the catheter 700 of FIG. 7. For example, other embodiments described herein may include one or more components of the imaging housing 728.

The imaging assembly illustrated in FIGS. 6-1 through 7 may be configured for a number of different imaging modalities. For example, the lenses 732 may be configured as part of the imaging assembly 606 that is a portion of a confocal microscope that may focus with a depth of 0-100 µm. In another example, the imaging assembly 606 may be a portion of a fluorescence microscope, multiphoton imaging system, optical coherence tomography system, or super-resolution optical imaging systems.

In some embodiments of an imaging assembly 606, the fiber-optic bundle 626, as well as the imaging housing 628, may have a diameter of between about 0.2 mm and about 5 mm. The fiber-optic bundle 626 may also have a length of between about 10 cm and about 10 m. In some embodiments, the imaging assembly 606 may be configured to produce and imaged of a selected tissue with a spatial resolution ranging from 1 µm to 100 µm. In other embodiments, the imaging assembly 606 may be configured to produce an image, image sequence or image stack of a selected tissue at a spatial resolution of less than about 4 µm. For example, the imaging assembly 606 may be configured to produce an image at a spatial resolution between 1.8 µm and 3.9 µm transverse to the direction of optical axis of the at least one lens 732.

Although described herein as comprising a fiber-optic bundle 626, the imaging assembly 606 may comprise any mechanism for transmitting an image from an objective lens 732 to an image processing system, including any known image-transmitting media. For example, the imaging assembly 606 may comprise at least one of a clear rod, a single wire, a plurality of wires, a microscopic camera, and the like, to effect transmission of an image as disclosed herein.

The imaging assembly 606 may be positioned in communication with a light source (not shown in FIGS. 6-1 and 6-2) that is configured for selective generation of light at a desired wavelength. This may allow for light of selected wavelengths to be selectively transmitted down the imaging assembly 606 and/or through the objective lens(es) 732. The objective lens(es) 732 may be configured to gather and focus reflected light from a selected tissue to produce an image of the selected tissue.

Figure 8:
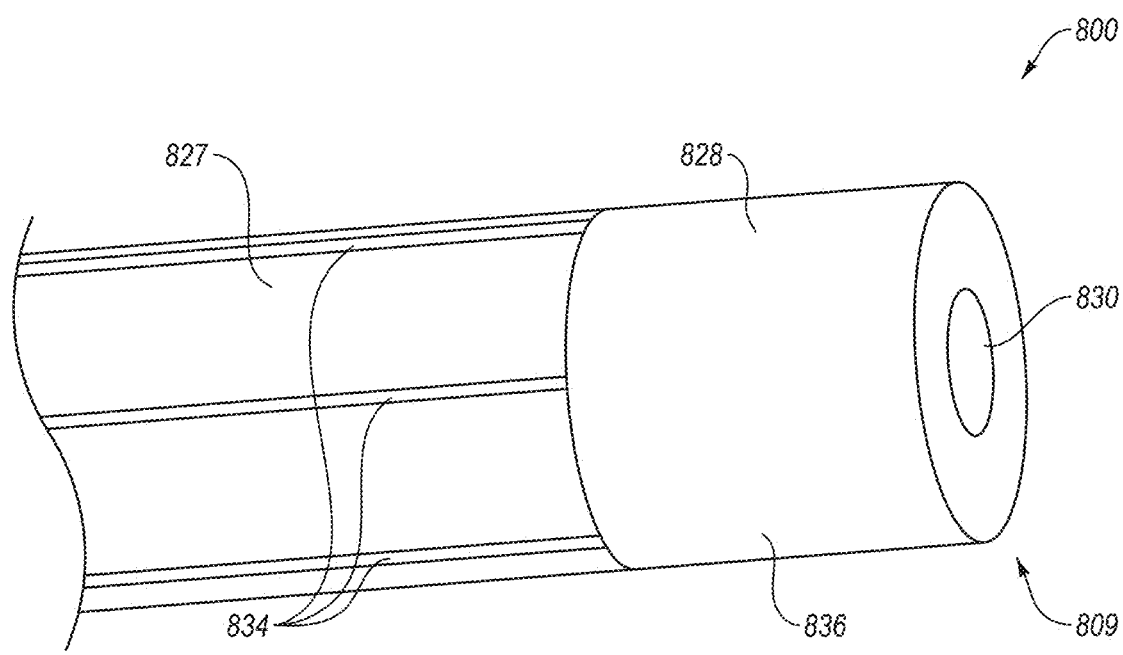
FIG. 8 illustrates an embodiment of a device for imaging and treating tissue with a dual-purpose housing.

FIG. 8 illustrates an embodiment of a catheter 800 for imaging and treating tissue. The catheter may include one or more of a fiber-optic bundle sheath 827, an imaging housing 828, an aperture 830, an energy application housing 836, and energy application wires 834. The energy application housing 836 and wires 834 may combine to form an energy application assembly. The fiber-optic bundle sheath 827, imaging housing 828, and aperture 830 may combine to form an imaging assembly. As shown in FIG. 8, the imaging housing 828 and energy application housing 836 are the same housing. In the illustrated embodiment, the imaging housing 828 is made of a conductive material. This conductive material may facilitate the transfer of energy to a selected tissue through the imaging housing 828 and therefore may also serve as an energy application housing 836. In this embodiment, as well as other embodiments herein described, this combined imaging and energy application housing may be referred to as a dual-purpose housing (e.g., including the imaging housing 828 and the energy application housing 836). The dual-purpose housing may be located at the distal tip 809 of the catheter 800.

Energy application wires 834, which may be in communication with the dual-purpose housing, may carry energy, such as electricity or heat, from a source (not shown) to the dual-purpose housing. FIG. 8 illustrates an embodiment in which three energy application wires 834 carry energy to the dual-purpose housing. Other embodiments may include more or fewer energy application wires 834. The energy application wires 834 may be made of conductive materials such as copper or other metals. The energy application wires 834 are shown as residing outside the fiber-optic bundle sheath 827. In other embodiments one or more energy application wires 834 may be at least partially located within and/or outside the fiber-optic bundle sheath 827. FIG. 8 does not show an outer sheath which may be placed over the energy application wires 834 to insulate them from exposure. In other embodiments, the fiber-optic bundle sheath 827 shown may be an outer sheath, the energy application wires 834 residing outside the outer sheath.

The energy application housing 836 and wires 834 are configured to apply energy to a selected tissue. This energy may be in the form of radiofrequency electrical waves, microwaves as well as heat and cold.

Components of other devices (e.g., for electrical mapping) may be incorporated into, and vice versa, the catheter 800 of FIG. 8. For example, other embodiments described herein may include one or more components of the dual-purpose housing.

Figure 9:
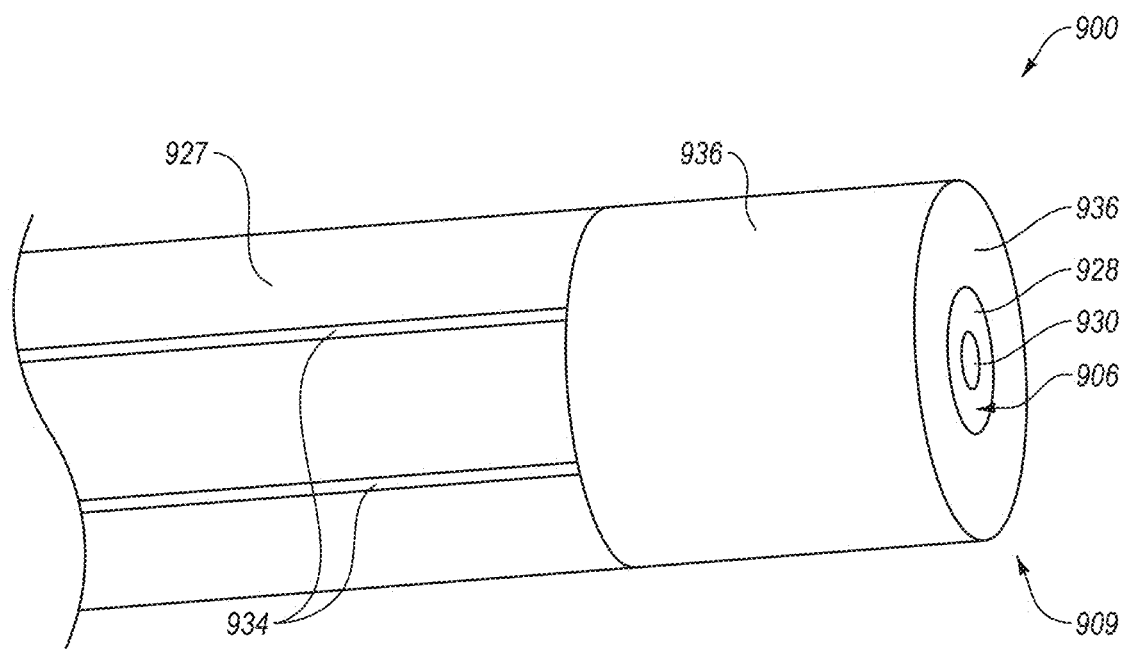
FIG. 9 illustrates an embodiment of a device for imaging and treating tissue with a separate imaging housing and energy application housing.

FIG. 9 illustrates an embodiment of a catheter 900 the imaging housing 928 and the energy application housing 936 are separate components. In the illustrated embodiment, the energy application housing 936 may circumferentially surround the imaging assembly 906. The imaging assembly 906 may be disposed within the energy application housing 936 but is exposed at a distal tip 909 of the catheter 900. The imaging assembly 906 may include an aperture 930. The imaging assembly 906 may be made of a rigid, insulating material. In this way, lens(es) (not shown) may be disposed within the imaging assembly 906 and may be insulated from energy supplied to the energy application housing 936 from the energy application wires 934. The energy application wires 934 may extend at least partially within the fiber-optic bundle sheath 927.

Components of other devices (e.g., for mapping) may be incorporated into, and vice versa, the catheter 900 of FIG. 9. For example, other embodiments described herein may include one or more components of the separate imaging housing 928 and the energy application housing 936.

Figure 10:
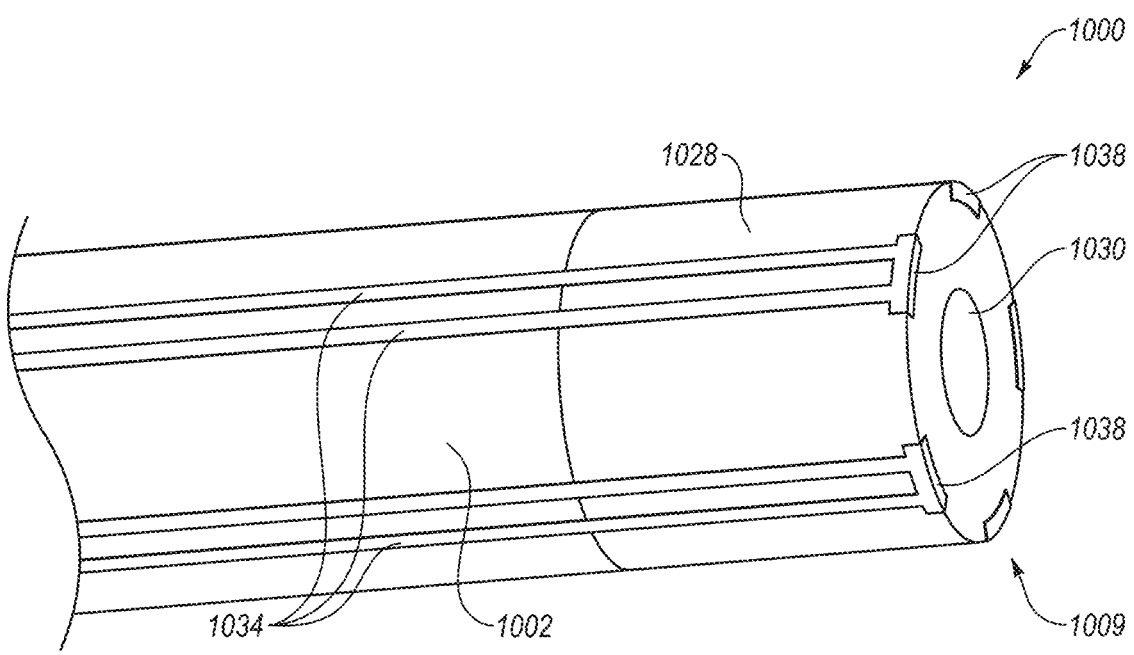
FIG. 10 illustrates an embodiment of a device for imaging and treating tissue with one or more energy application zones.

FIG. 10 illustrates an embodiment of catheter 1000 (e.g., a device) for imaging, treating, and/or mapping tissue that includes an outer sheath 1002. The catheter 1000 may include an imaging housing 1028, an aperture 1030, energy application wires 1034, and multiple energy application zones 1038. The energy application zones 1038 may be configured so that at least a portion of the energy application zones 1038 are exposed on the distal tip 1009 of the catheter 1000. Energy application wires 1034 may be in communication with each energy application zone 1038 to provide energy to the energy application zones 1038. As shown, each energy application zone 1038 may have a corresponding energy application wire 1034. In other embodiments, each energy application wire 1034 may be in communication with one or more energy application zones 1038. The energy application zones 1038 are made of a conductive material suitable to conduct and/or transfer energy to a selected tissue. The illustrated embodiment includes five energy application zones 1038, but other embodiments may include more or fewer than five.

Components of the other devices (e.g., catheters) described herein may be incorporated into, and vice versa, the catheter 1000 of FIG. 10. For example, other embodiments described herein may include one or more components of the catheter 1000 including one or more energy application zones.

Figure 11:
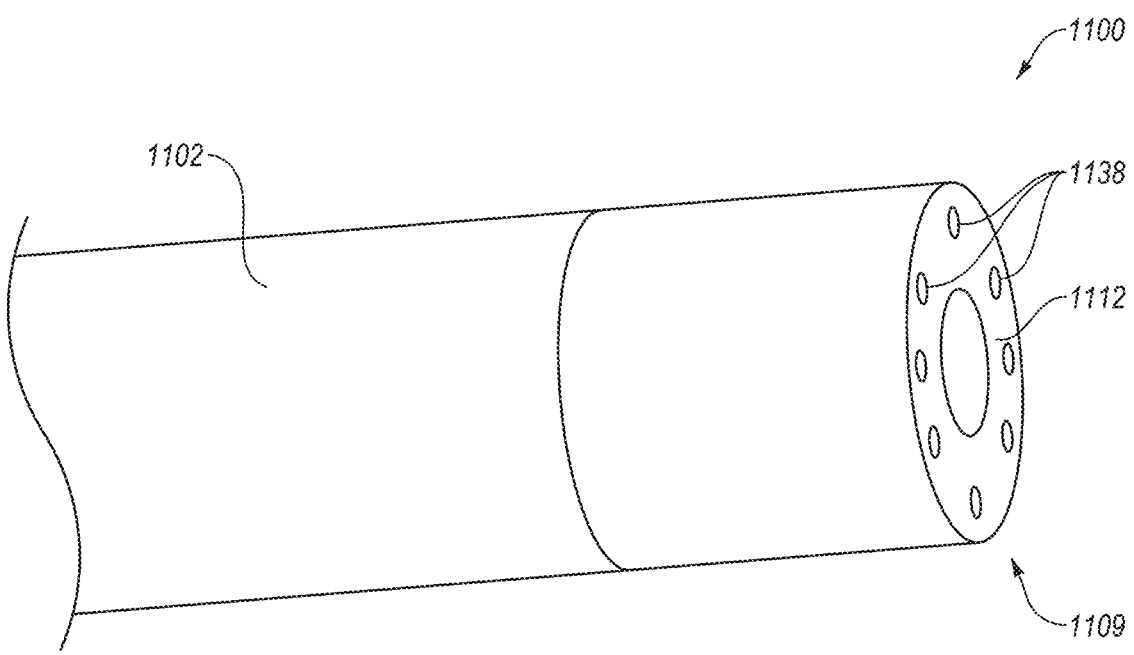
FIG. 11 illustrates another embodiment of a catheter for imaging and treating tissue with one or more energy application zones.

FIG. 11 illustrates another embodiment of a catheter 1100 for imaging, treating, and/or mapping tissue that includes an outer sheath 1102, an imaging aperture 1112, and multiple energy application zones 1138 disposed on a distal end 1109 of the catheter 1100. The illustrated embodiment includes seven energy application zones 1138. Other embodiments may include more or less than seven energy application zones 1138. The energy application zones 1138 illustrated are circular in shape, but they may be any shape. The circular energy application zones 1138 illustrated may have outer diameters ranging from about 1 mm to about 5 mm. One or more of the energy application zones 1138 may be disposed on the distal tip 1109 (e.g., a dual-purpose housing, an imaging housing, an energy application housing, or combinations thereof) as shown.

The energy application housings 836, 936, 1236, 1336, 1436, 1836, described herein, which may or may not be the same component as the imaging housings 528, 628, 728, 828, 928, 1028, 1228, 1328, 1428, described herein, and energy application zones 1038, 1138 described herein, are configured to supply energy to a selected tissue. The energy applied may ablate the selected tissue. The energy application housings and energy application zones may comprise platinum-iridium tip electrodes or gold-tip electrodes. However, any energy application electrodes, including conventional ablation electrodes, may be used.

Components of other devices (e.g., for mapping) may be incorporated into, and vice versa, the catheter 1100 of FIG. 11. For example, other embodiments described herein may include energy application zones 1138.

Figures 1, 12:
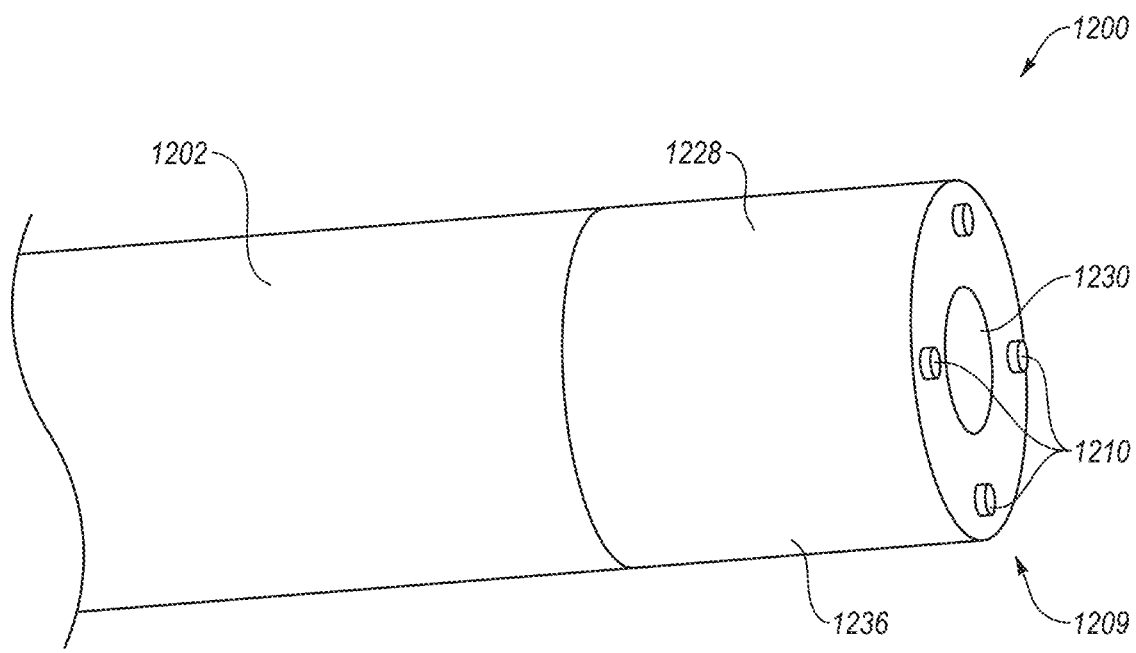
Figures 2, 12:
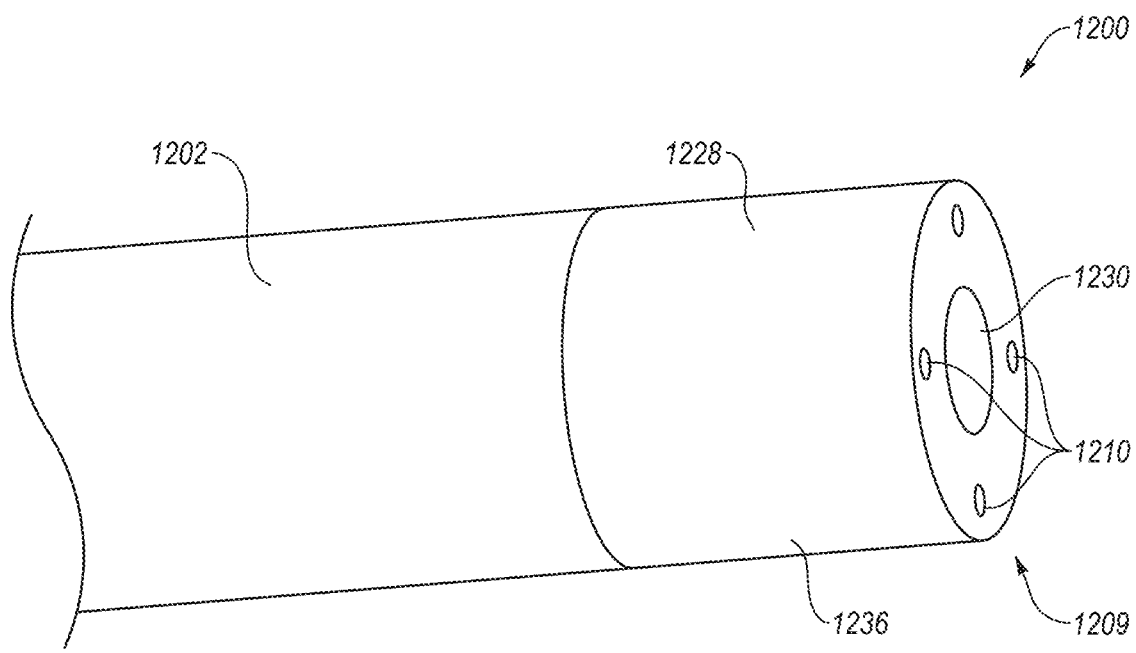

FIG. 12-1 illustrates an embodiment of a catheter 1200 for treating tissue with multiple mapping electrodes 1210. The catheter 1200 may include an outer sheath 1202, a dual-purpose housing (e.g., including an imaging housing 1228 and an energy application housing 1236), and an imaging aperture 1230. The illustrated embodiment includes four mapping electrodes 1210 circumferentially spaced around the distal tip 1209 of the catheter. Other embodiments may include more or fewer than four mapping electrodes 1210. The mapping electrodes 1210 may extrude from the distal tip 1209 of the catheter 1200 and are configured to come into contact with, or at least come in close proximity to, a selected tissue. The mapping electrodes 1210 may be configured to record electrical activity of a selected tissue.

As shown in FIG. 12-1, the mapping electrodes may extend out from the distal tip 1209 of the catheter 1200. As shown in FIG. 12-2, the mapping electrodes 1210 may be flush with the distal tip 1209. The mapping electrodes 1210 illustrated in FIGS. 12-1 and 12-2 may be fixed in position and/or moveable, may be flush and/or extruded, or combinations thereof. For example, one or more of the mapping electrodes 1210 may reside in ports (not shown) and selectively advance from inside the catheter 1200 to extrude outward beyond the distal tip 1209 of the catheter 1200.

It is contemplated that each mapping electrode 1210 of the plurality of mapping electrodes 1210 of the mapping assembly (not shown) may be configured to record electrical activity within a selected tissue. In some embodiments, each respective mapping electrode of the plurality of mapping electrodes 1210 may include a steel electrode, a stainless steel electrode, a silver-silver-chloride electrode, other electrodes, or combinations thereof.

The mapping electrodes 1210 are configured to record electrical signals from a selected tissue. Such electrical signals reflect conduction pathways and disturbances including arrhythmia as well as cellular activity and dysfunction. Measurements of the mapping electrodes include electric potentials, impedance, and/or resistance of a selected tissue.

Components of other devices (e.g., for imaging, treating (e.g., ablating and/or delivering drug), and/or mapping) may be incorporated into, and vice versa, the catheter 1200 of FIG. 12. For example, other embodiments described herein may include one or more components of the mapping electrodes 1210.

Figures 1, 13:
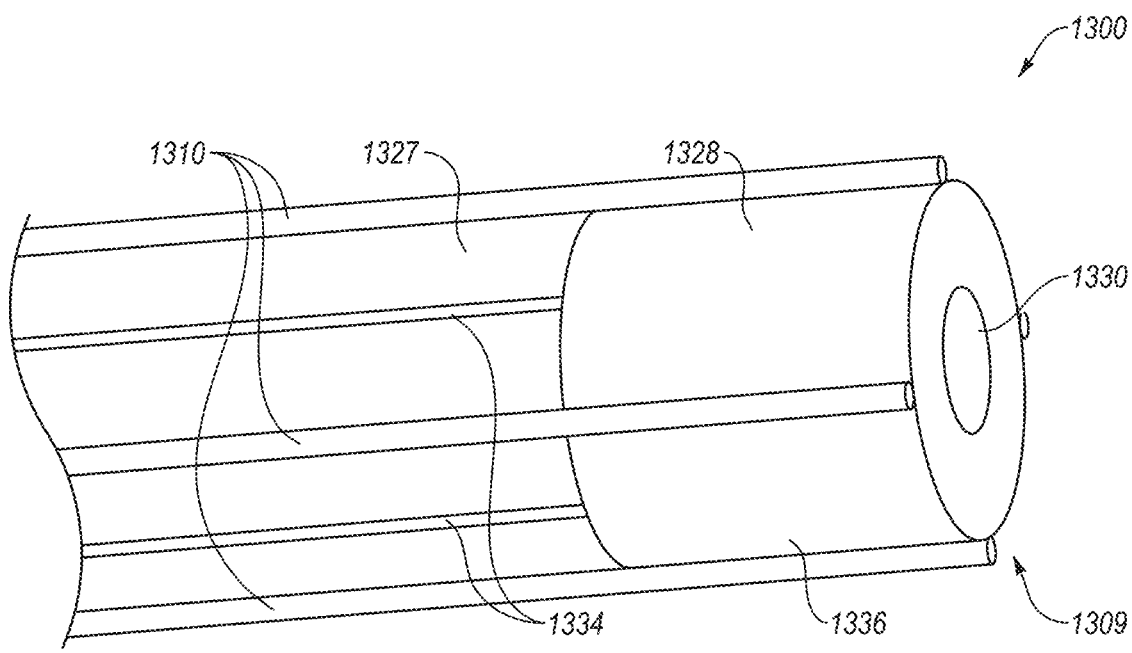
Figures 2, 13:
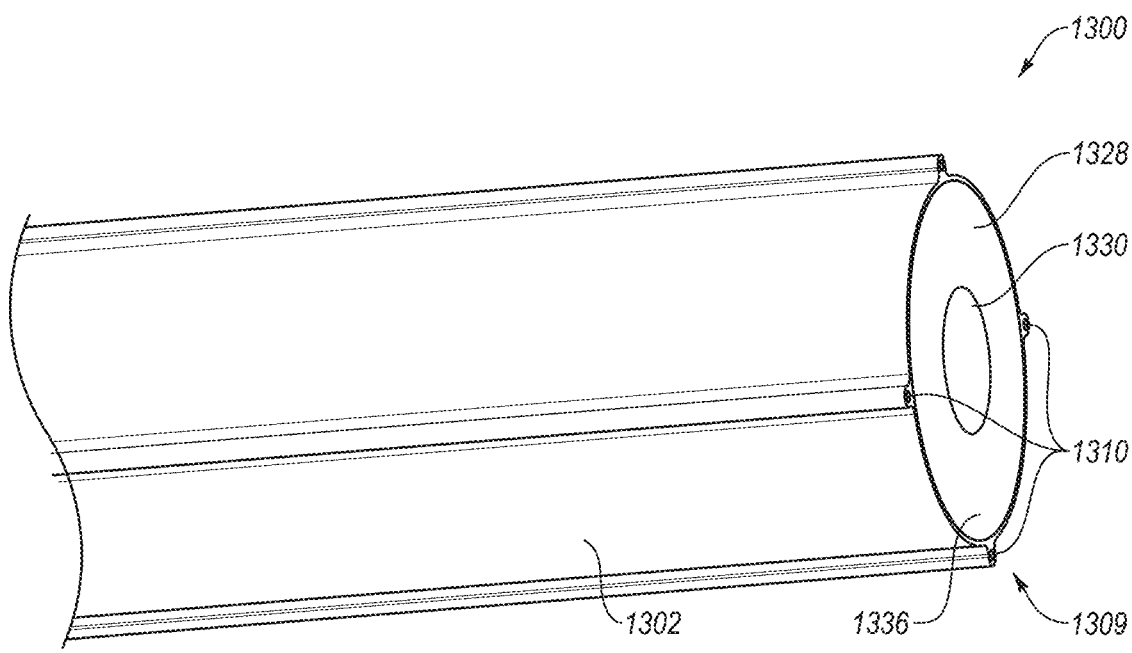

FIGS. 13-1 and 13-2 illustrate an embodiment of a catheter 1300 for imaging treating, and/or mapping tissue that includes a dual-purpose housing (e.g., including an imaging assembly housing 1328 and an energy application assembly housing 1336), energy application wires 1334, an imaging aperture 1330, and mapping electrodes 1310. The imaging assembly housing 1328 may include a fiber-optic bundle sheath 1327.

The mapping electrodes 1310 may be disposed on the outer circumference of the catheter 1300 and extend to a distal tip 1309 of the catheter 1300. FIG. 13-2 illustrates the same embodiment as FIG. 13-1, but with an outer sheath 1302. FIGS. 13-1 and 13-2 illustrate four mapping electrodes 1310. Other embodiments may include more or fewer than four mapping electrodes 1310.

Mapping electrodes 1310 may be selectively advanced through ports (e.g., port 212, 312, 412, 1112) and may be independently steerable. Other embodiments may include other configurations of mapping electrodes 1310 and/or modes of operability. Other configurations of mapping electrodes 1310 and/or deployment modalities may also be used in the embodiments herein described and/or other embodiments.

Components of other devices (e.g., for imaging, treating (e.g., ablating and/or delivering drug), and/or mapping) may be incorporated into, and vice versa, the catheter 1300 of FIGS. 13-1 and 13-2. For example, other embodiments described herein may include one or more components of the mapping electrodes 1310.

Figures 1, 14:
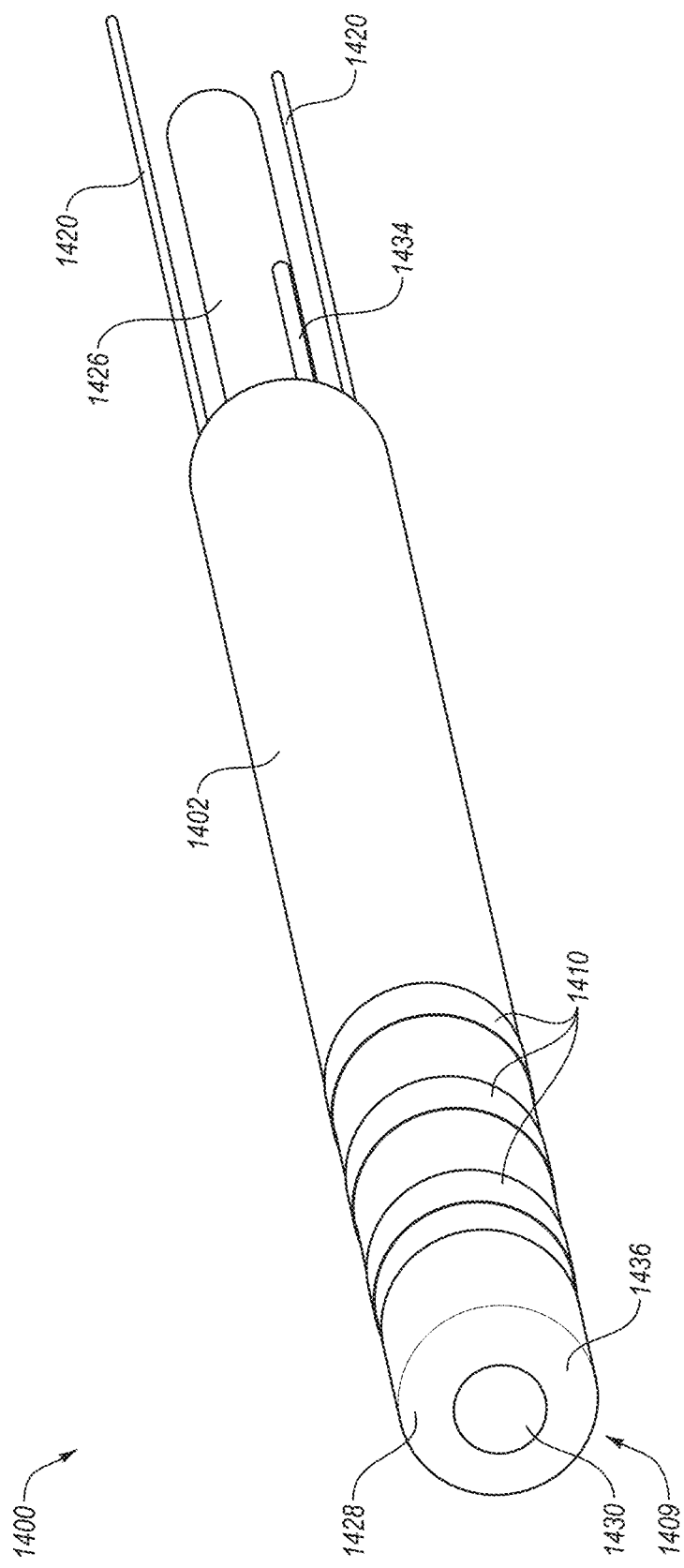
Figures 2, 14:
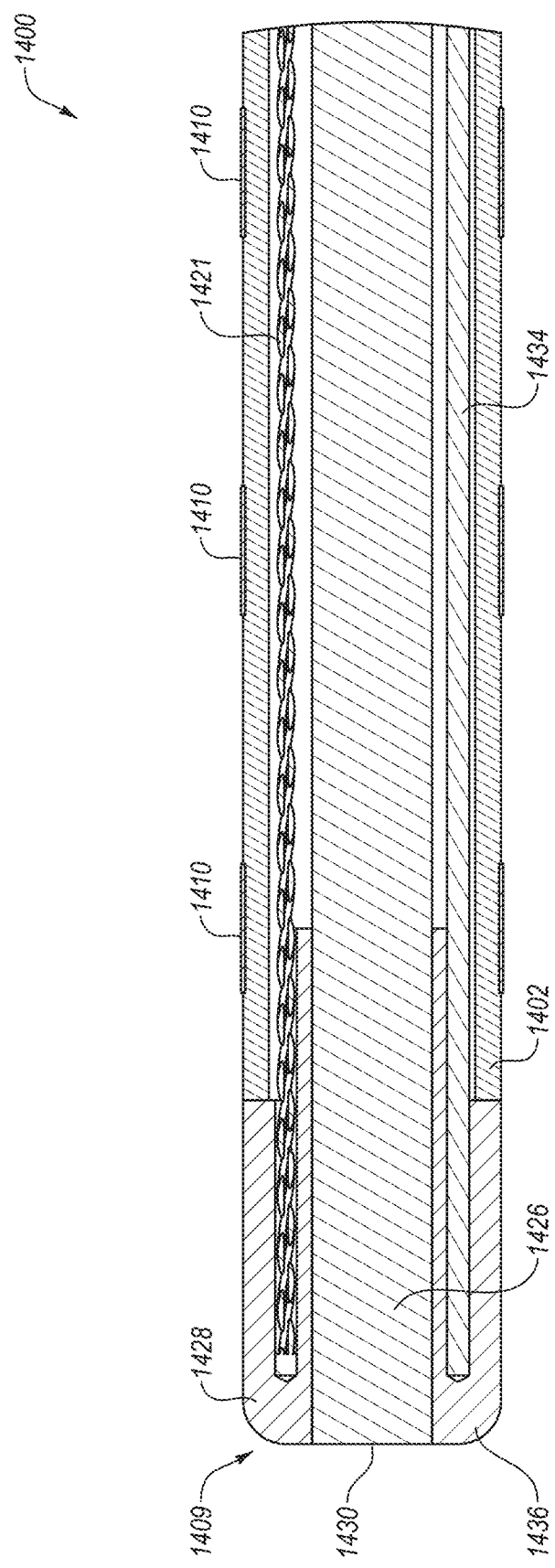

FIGS. 14-1 and 14-2 illustrate an embodiment of a catheter 1400 for imaging, treating, and/or mapping tissue where imaging, mapping, and treatment (e.g., energy application and/or drug delivery) assemblies are co-located at a distal end 1409 of the catheter 1400. The imaging assembly includes a dual-purpose housing (e.g., including an imaging assembly housing 1428 and an energy application assembly housing 1436), imaging aperture 1430, and fiber-optic bundle 1426. The energy ablation assembly includes a dual-purpose housing and one or more energy application wires 1434. The mapping assembly, as illustrated, includes three mapping electrodes 1410 disposed as rings around the circumference of the outer sheath 1402. In other embodiments, the mapping assembly may include more or fewer than three mapping electrodes 1410 one or more of which may be rings. Actuation wires 1420 are also shown.

FIG. 14-2 illustrates a cross-sectional view of an embodiment of a catheter 1400 for imaging and treating a selected tissue. In this embodiment, the catheter 1400 may include one or more components of the various catheters described herein, but is illustrated with an outer sheath 1402, mapping electrodes 1410, a fiber-optic bundle 1426, an imaging aperture 1430, a dual purpose housing (e.g., including an imaging assembly housing 1428 and an energy application assembly housing 1436), and thermistor wires 1421. The thermistor wires 1421 may extend longitudinally along the inside of the outer sheath 1402 and/or may extend to a distal tip 1409 of the catheter 1400. The thermistor wires are configured to sense a temperature at the distal tip 1409 of the catheter 1400.

The embodiment illustrated in FIGS. 14-1 and 14-2 is an example of a catheter 1400 that may image, map, and apply energy to a selected tissue from a single instrument. Portions of the imaging, mapping, and energy application assemblies are co-located at the distal end 1409 of the catheter 1400 in a neatly packed and functional manner. This allows a doctor or other operator of the catheter 1400 to perform the imaging, mapping, and treating functions to a selected tissue without the need for any outside instrumentation.

Components of other devices (e.g., for imaging, treating (e.g., ablating and/or delivering drug), and/or mapping) may be incorporated into, and vice versa, the catheter 1400 of FIGS. 14-1 and 14-2. For example, other embodiments described herein may include one or more components of the energy application assembly.

A method for treating a selected tissue of a subject, such as a portion of an interior surface of the interior tissue of a heart, may include imaging, mapping, and treating the selected tissue. In one or more embodiments, the imaging, mapping, and treating may be done simultaneously. In at least one embodiment, the imaging, mapping, and treating steps performed on the selected tissue may be done using a single instrument, such as one or more of the catheters herein described. In at least one embodiment, it may not be necessary to withdraw and insert multiple instruments and/or catheters in order to perform these different steps. The imaging, mapping, and treating (e.g., ablating and/or delivering drug) of selected tissue may be performed from the interior of a subject, such as the interior of a heart or other organ, in order to effectively treat (e.g., ablate and/or deliver drug) a selected tissue, such as the interior wall of a heart or other organ tissue.

Figures 1, 15:
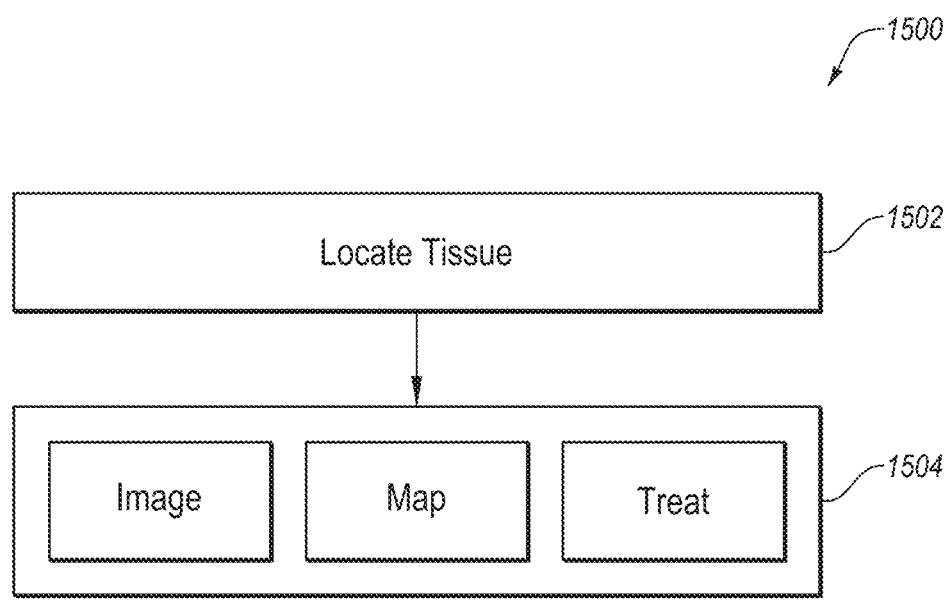
Figures 2, 15:
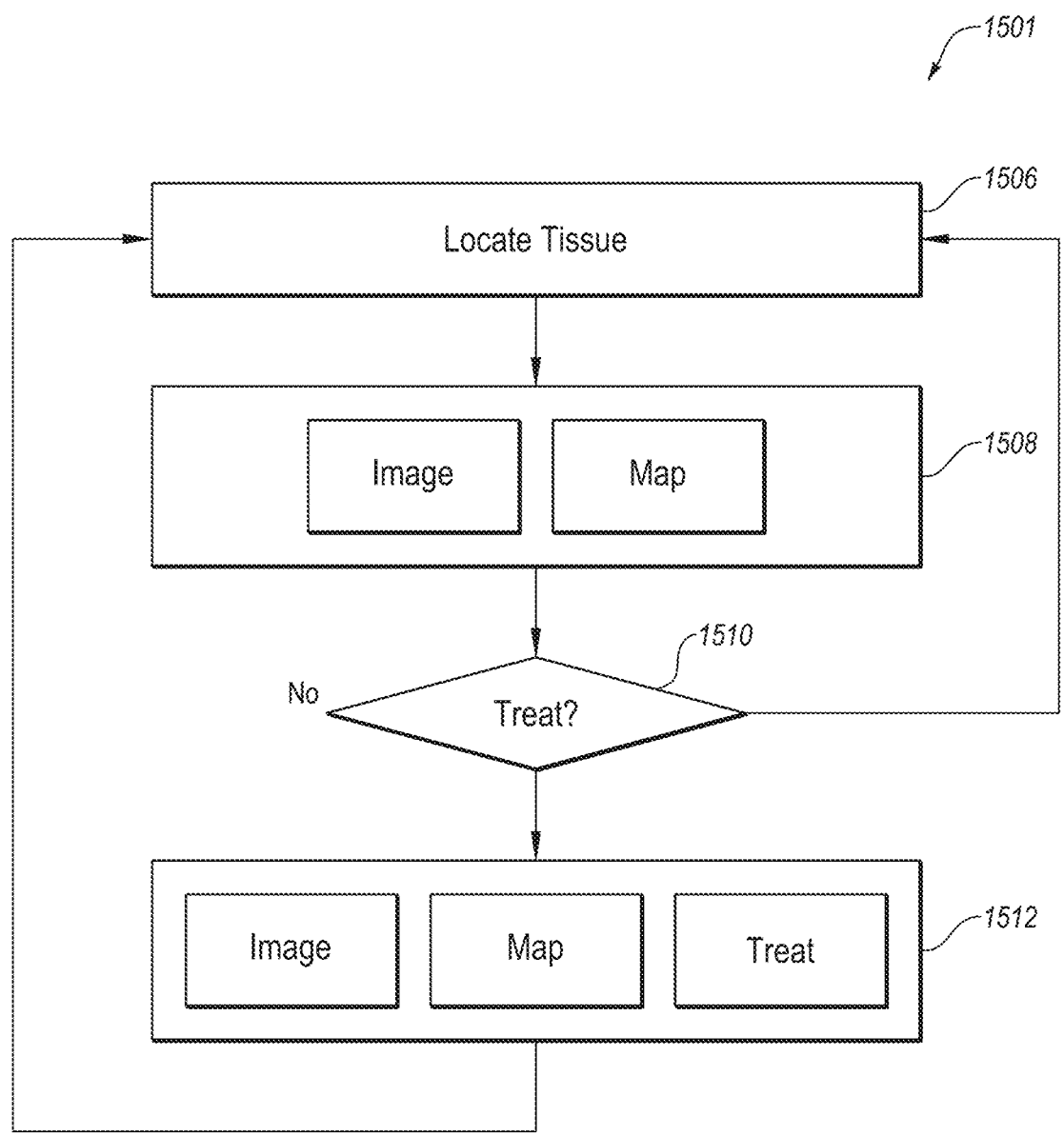

FIG. 15-1 illustrates a flowchart of a method 1500 of treating a selected tissue. The method 1500 includes the act 1502 of locating tissue. Once the catheter has been inserted as desired, and a selected tissue has been located 1502, the selected tissue may be imaged, treated (e.g., ablated and/or deliver drug), and/or mapped simultaneously 1504. In some embodiments, in addition or in alternative to ablating, a drug may be delivered, as described herein. Thus, in some embodiments, the selected tissue may be imaged and ablated; imaged and mapped; imaged, ablated, and mapped; imaged and have a drug delivered; imaged, ablated, and have a drug delivered; imaged, mapped, and have a drug delivered; or imaged, ablated, mapped, and have a drug delivered. Thus, the selected tissue may be treated by ablation and/or drug delivery.

The insertion of a catheter and the locating 1502 of a selected tissue is described in more detail below in reference to FIG. 17. The imaging assembly of the catheter herein described may provide a live feed image of the selected tissue while treatment (e.g., ablation and/or drug delivery) occurs. Mapping may also provide live electrical information feedback of the tissue, as described herein, while treatment (e.g., ablation and/or drug delivery) is occurring. The live imaging and mapping of the tissue during treatment (ablation and/or drug delivery) may provide outputs to a processor and/or operator. The processor and/or operator may continue treatment (e.g., ablation and/or drug delivery) or determine that the tissue has been sufficiently ablated and/or sufficient drugs have been delivered based on those outputs.

An energy application assembly of a catheter as described herein may apply radiofrequency energy to the selected tissue in order to ablate the tissue. Radiofrequency energy is one example of energy that may be applied to the selected tissue. Other examples of applied energy may include microwaves as well as heat and cold The energy applied to the selected tissue may increase or decrease the temperature of the tissue to a point where the cells within the tissue die, thus ablating the tissue.

A drug delivery assembly of a catheter as described herein may deliver a drug to treat a selected tissue. Treating a selected tissue may include providing a beneficial or deleterious agent to the selected tissue. For example, the one or more agents may be delivered may include, but are not limited to, beneficial agents such as cytotoxins, antifibrotic drugs, anti-inflammatory drugs, ion channels blockers and activators, cytokines, other drugs, or combinations thereof and/or deleterious agents, such as, tissue ablating agents, including, but not limited to, alcohol.

Components of the other methods described herein may be incorporated into, and vice versa, the method 1500 of FIG. 15-1. For example, other embodiments described herein may include imaging, mapping, ablating, drug delivery, or combinations thereof 1504.

FIG. 15-2 illustrates another method 1501 of treating a selected tissue, such as those herein described. As shown, a selected tissue is first located 1506 in a similar fashion as described above in reference to FIG. 15-1. The method 1501 includes imaging and/or mapping 1508 the selected tissue after it has been located, but before treatment (e.g., ablation and/or drug delivery) is performed. These steps may occur simultaneously or in succession. The first imaging and/or mapping 1506 may provide initial outputs which may be received by a processor and/or operator of the catheter to determine 1510 whether treatment (e.g., ablation and/or drug delivery) is appropriate. Treatment may not be appropriate, for example, if the selected tissue comprises a critical nerve that may need to be preserved. If the processor and/or operator of the catheter determines, based on the initial imaging and/or mapping outputs, that treatment of the selected tissue is desired, then treatment may be performed using an ablation assembly and/or drug delivery assembly of a catheter as herein described.

Imaging and/or mapping of the selected tissue while treatment is occurring 1512 may provide a second set of outputs to the processor and/or operator of the catheter. These second set of outputs may be used to determine whether sufficient treatment (e.g., sufficient ablation and/or sufficient drug delivery) has occurred and when to stop treatment. Once treatment has been performed, the tissue may then be imaged and/or mapped again 1508, as shown in FIG. 15-2. These acts may continue until the selected tissue is sufficiently treated (e.g., act 1510). Afterward, another selected tissue may be located 1506 to perform the foregoing steps as illustrated in FIG. 15-2.

Components of the other methods described herein may be incorporated into, and vice versa, the method 1501 of FIG. 15-2. For example, other embodiments described herein may include simultaneous imaging and/or mapping 1508 and then determining 1510 whether to treat before treatment.

Figure 16:
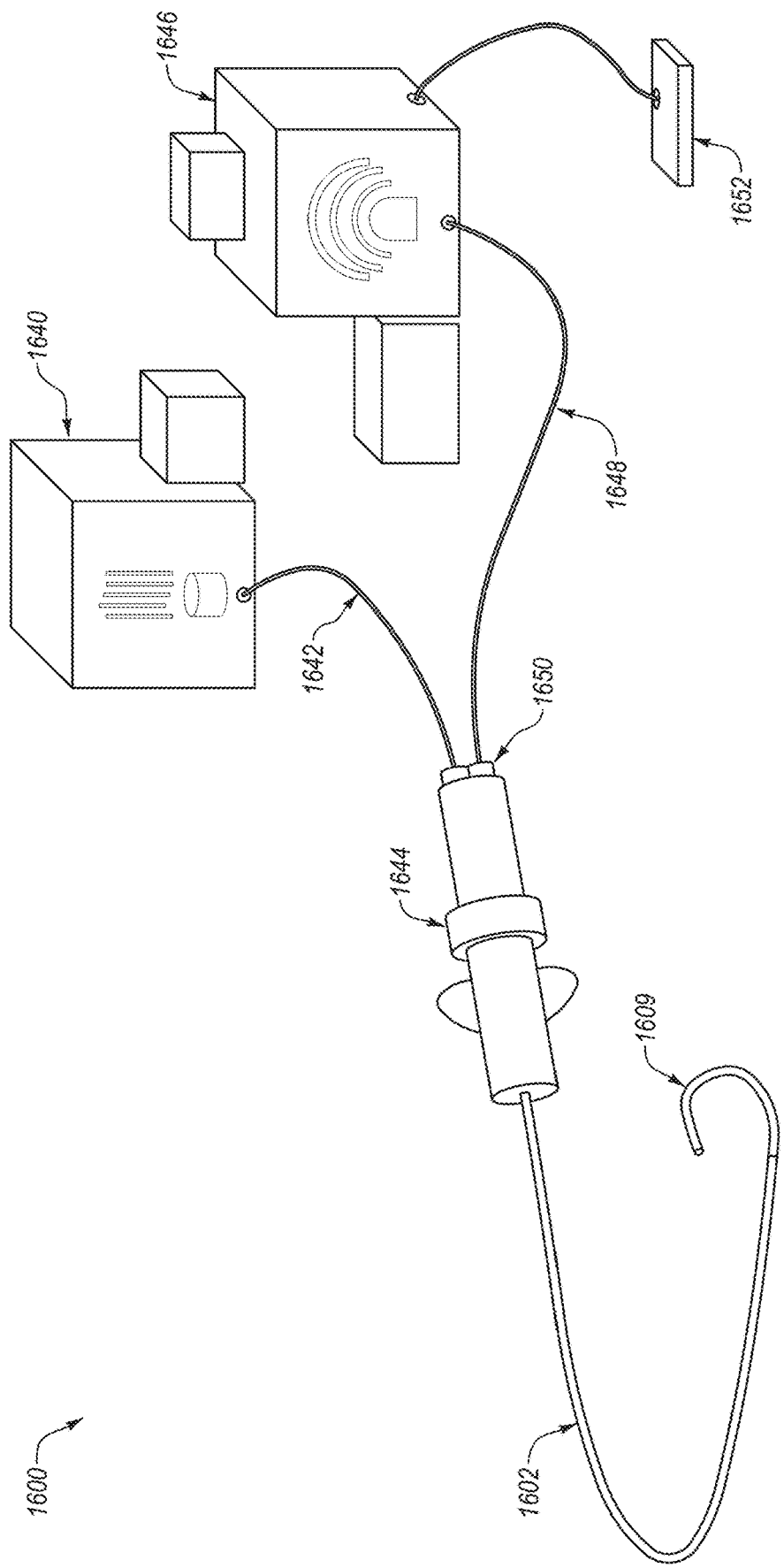
FIG. 16 illustrates an overall schematic of an embodiment of a catheter system for imaging and treating a selected tissue.

FIG. 16 illustrates an overall schematic of an embodiment of a catheter system 1600 for imaging and treating (e.g., ablating and/or delivering drug) a selected tissue. The system may be used to perform various steps of the method described herein. A mapping system component is not shown in this embodiment, but may also be included in this or other embodiments herein described. The catheter system 1600 of the illustrated embodiment may include an outer sheath 1602 and a steerable distal tip 1609.

A fiber-optic confocal microscope (FCM) system 1640 may be included as an imaging assembly. The FCM may include an FCM probe fiber 1642. The FCM system 1640 may be in communication with a control wand 1644 of the catheter 1600 via the FCM probe fiber 1642. The FCM system 1640 may be configured to provide a light source and light detector components (not shown) that may be in communication with a fiber-optic bundle (not shown) of the catheter system 1600. Other imaging systems may also be provided. For example, the imaging system may be a fluorescent microscope system. Other systems may include, but are not limited to, fluorescence microscope, multiphoton imaging system, optical coherence tomography system, and super-resolution optical imaging systems.

A radiofrequency (RF) ablation system 1646 may be provided as an energy ablation assembly. The RF ablation system 1646 may include an RF connector cable 1648. The RF ablation system 1646 may be in communication with the catheter system 1600 via the RF connector cable 1648. The RF connector cable 1648 may be attached to the control wand 1644 via a RF multi-pin connector 1650. The RF ablation system 1646 may supply radiofrequency energy to an energy application assembly (not shown) of the catheter system 1600. An actuator 1652 (e.g., a foot control) may be provided and configured to selectively activate the RF ablation system 1646 when ablation of a selected tissue is desired.

In some embodiments in addition to or instead of the energy application assembly a drug delivery assembly may be used. The drug delivery assembly may include a lumen through which various agents may be delivered. The agents that may be delivered may include, but are not limited to, beneficial agents such as cytotoxins, antifibrotic drugs, anti-inflammatory drugs, ion channels blockers and activators, cytokines, other drugs, or combinations thereof and/or tissue ablating agents, such as alcohol.

Components of other devices (e.g., for imaging, treating (e.g., ablating and/or delivering drug), and/or mapping) may be incorporated into, and vice versa, the catheter system 1600 of FIG. 16. For example, the catheter system 1600 may include one or more components of the catheters described herein.

Figure 17:
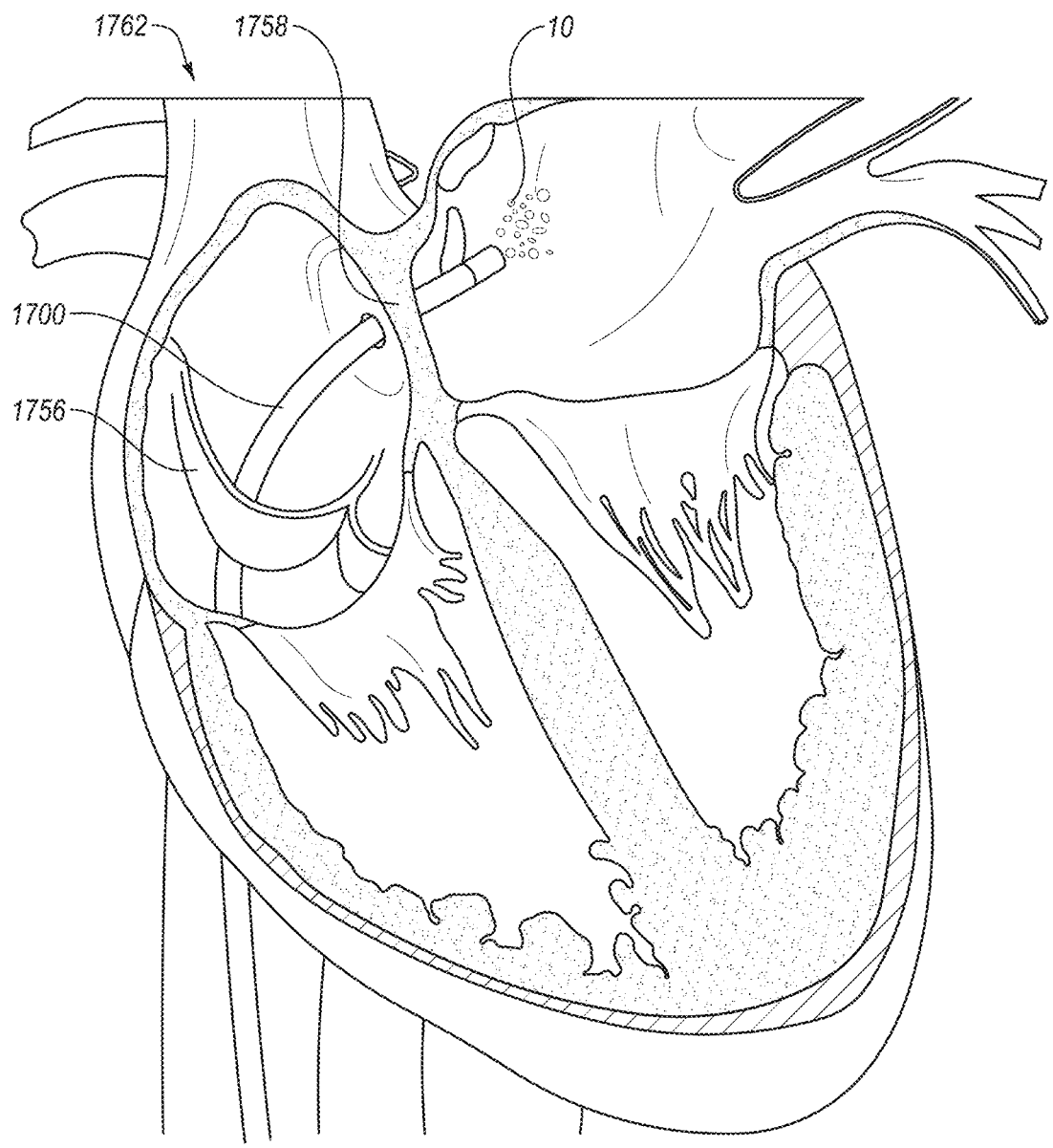
FIG. 17 illustrates a method of locating a selected tissue.

FIG. 17 illustrates a method of locating a selected tissue. For example, a catheter 1700 may be inserted into blood vessels and through the inferior vena cava. Components of the other devices (e.g., catheters) described herein may be incorporated into, and vice versa, the catheter 1700 of FIG. 17.

The catheter 1700 may be advanced through blood vessels and a right atrium 1756, across an atrial septum 1758 and into a left atrium 1760. A selected tissue 10 to treat (e.g., ablate and/or deliver drug) may be on an interior portion of the left atrium 1760. The selected tissue 10 may be the interior cardiac tissue of a blood-filled, beating heart 1762. Cardiac tissue is one example of tissue that may be selected for treatment (e.g., ablation and/or drug delivery). Other examples of selected tissues may include, but are not limited to, pulmonary, gastrointestinal, urogynecologic, endocrine, neural and vascular tissues.

As the catheter 1700 is inserted into a subject, the imaging assembly may be producing images and/or image sequences of the interior of the subject. These images and/or image sequences may assist an operator, such as a doctor, in viewing and locating a selected tissue as the catheter is being inserted. The catheter 1700 may map the tissue inside of the subject as it is being inserted, further characterizing the tissue and assisting in locating the tissue and positioning the mapping and treatment (e.g., ablation and/or drug delivery) devices.

The catheter 1700 may be steered and/or bent using actuation wires, as described herein, in order to navigate within a subject to reach the selected tissue 10. In other embodiments, the catheter 1700 may be inserted into a left atrium 1756 of a heart 1762 so that a distal end of the catheter 1700 is in close proximity to a portion of selected tissue without steering or using the actuation wires. For example, a steerable guide catheter may be used. Once the distal tip of the catheter 1700 is in close proximity to the selected tissue 10, the actuation wires may be used to bend the catheter 1700 so that the distal end of the catheter 1700 comes in contact with the selected tissue 10.

Figures 1, 18:
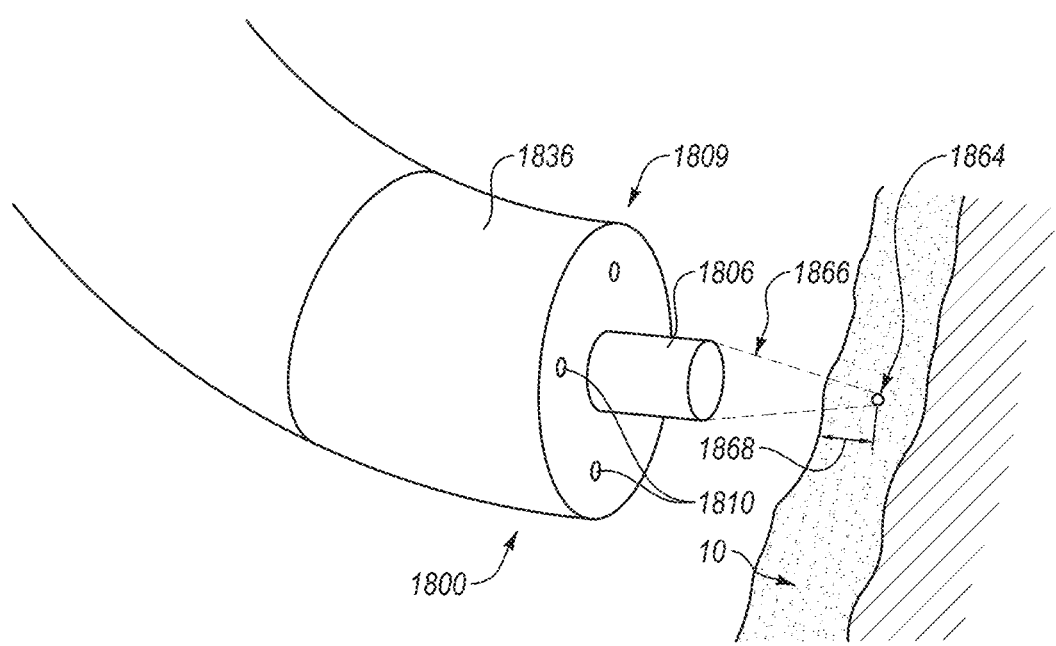
Figures 2, 18:
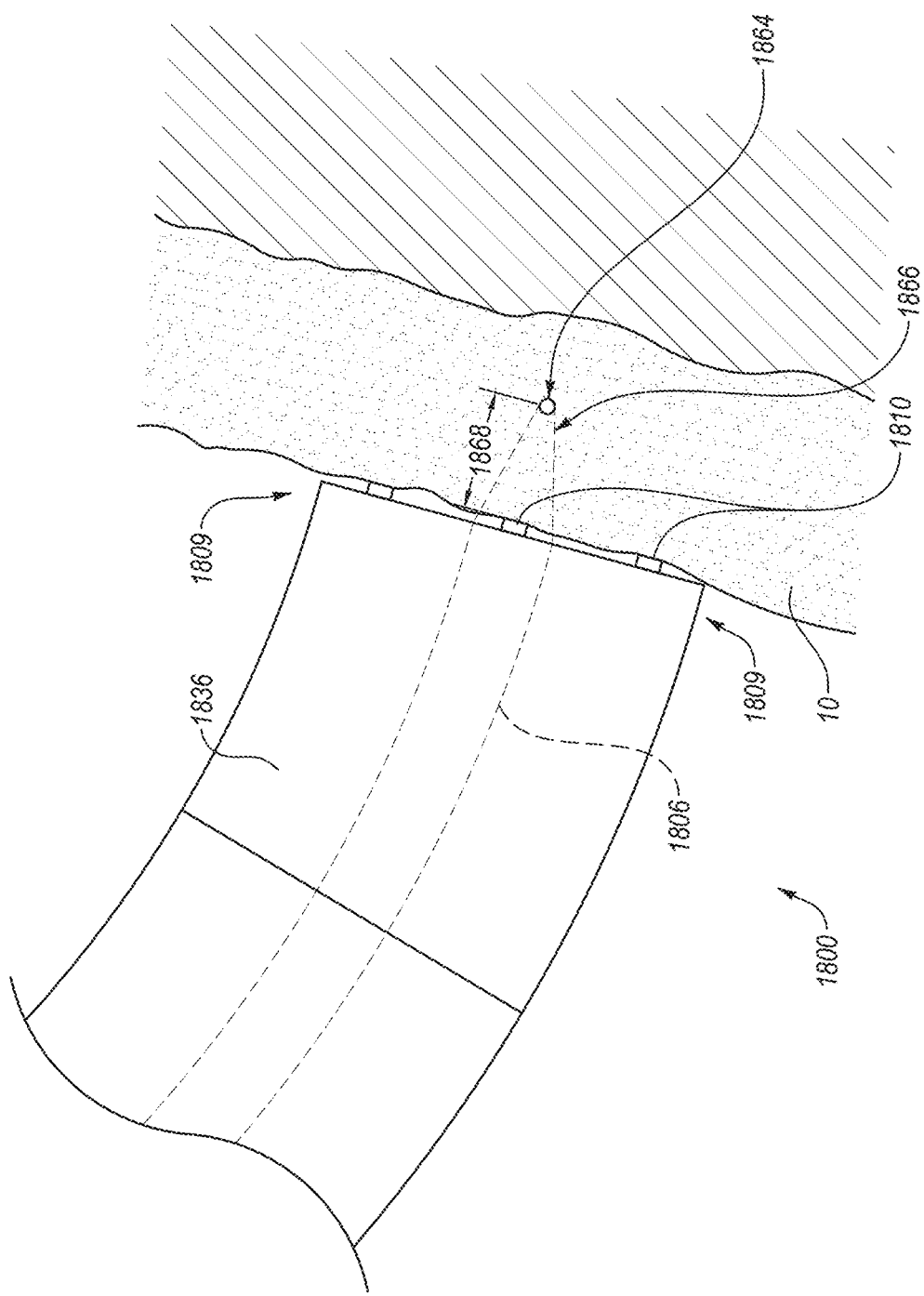

FIGS. 18-1 and 18-2 illustrate an embodiment of a catheter 1800 performing an imaging step of the method for treating (e.g., ablating and/or delivering drug) a selected tissue herein described. Components of other devices (e.g., for imaging, treating (e.g., ablating and/or delivering drug), and/or mapping) may be incorporated into, and vice versa, the catheter 1800 of FIG. 18.

The catheter 1800 may include a mapping assembly 1810, an energy application housing 1836, and a confocal microscope imaging assembly 1806. The light path 1866 is emitted from the confocal microscope imaging assembly 1806 may be such that a focal point 1864 may be located within a depth of the selected tissue 10. The confocal microscope imaging assembly 1806 may provide a depth of focus of 25 to 100 μm beneath the tissue 10 surface.

The imaging assembly 1806 and mapping assembly 1810 of the catheter 1800 may be in direct contact with the selected tissue 10. In some embodiment the imaging assembly 1806 may not be advanced beyond the distal tip 1809 of the catheter 1800, but may still provide an image of the tissue 10 as it resides within the catheter 1800.

Figure 19:
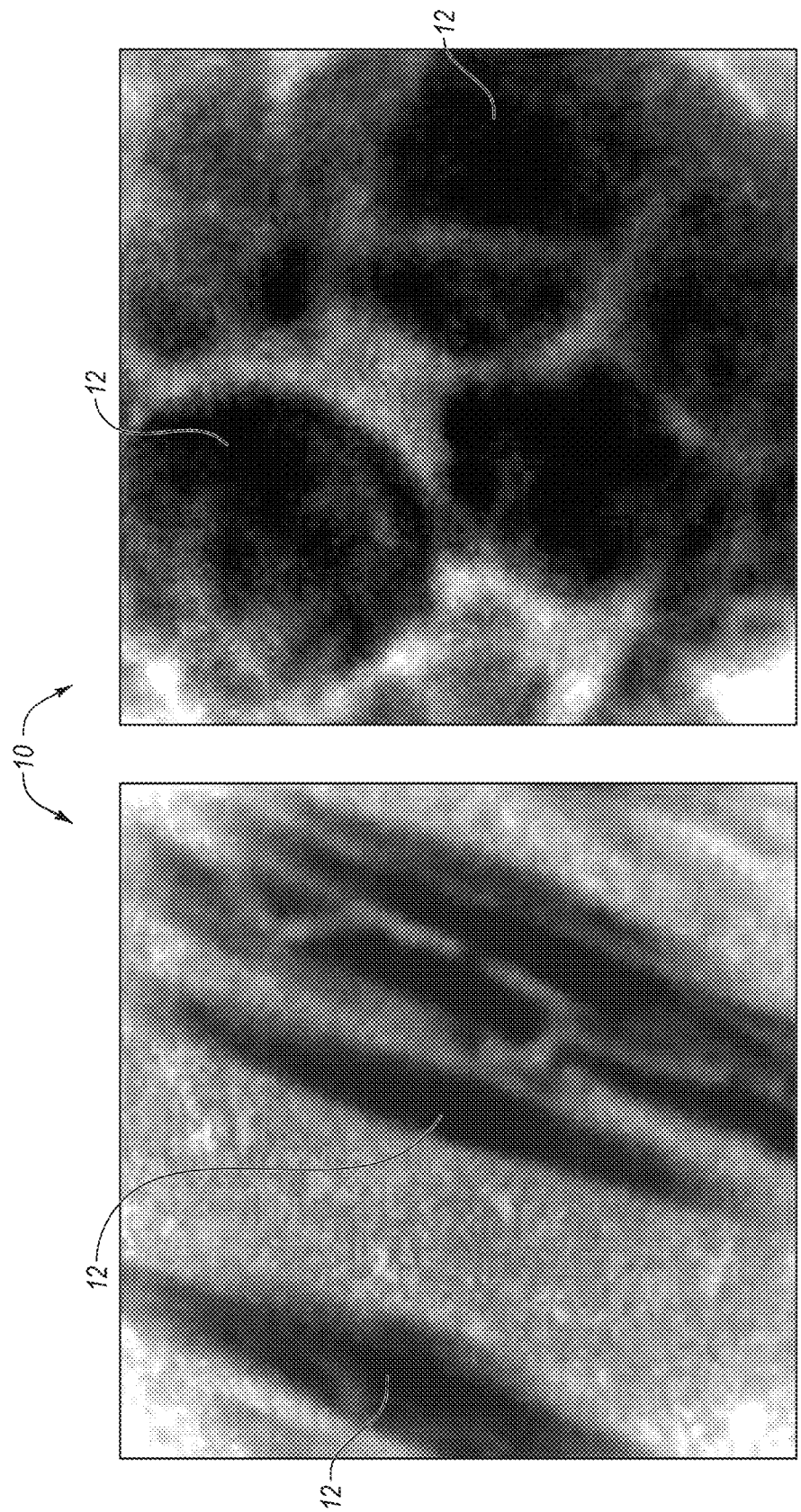
FIG. 19 illustrates an example images of selected tissue that has been treated (e.g., ablated)

FIG. 19 illustrates example images of selected tissue 10 that has been ablated. Images were acquired using fiberoptics confocal microscopy after application of a fluorescent maker of the cell exterior. The darker portions of the images represent ablated tissue constituents 12. The selected tissue 10 of FIG. 19 was ablated using an embodiment of a catheter as described herein.

Figure 20:
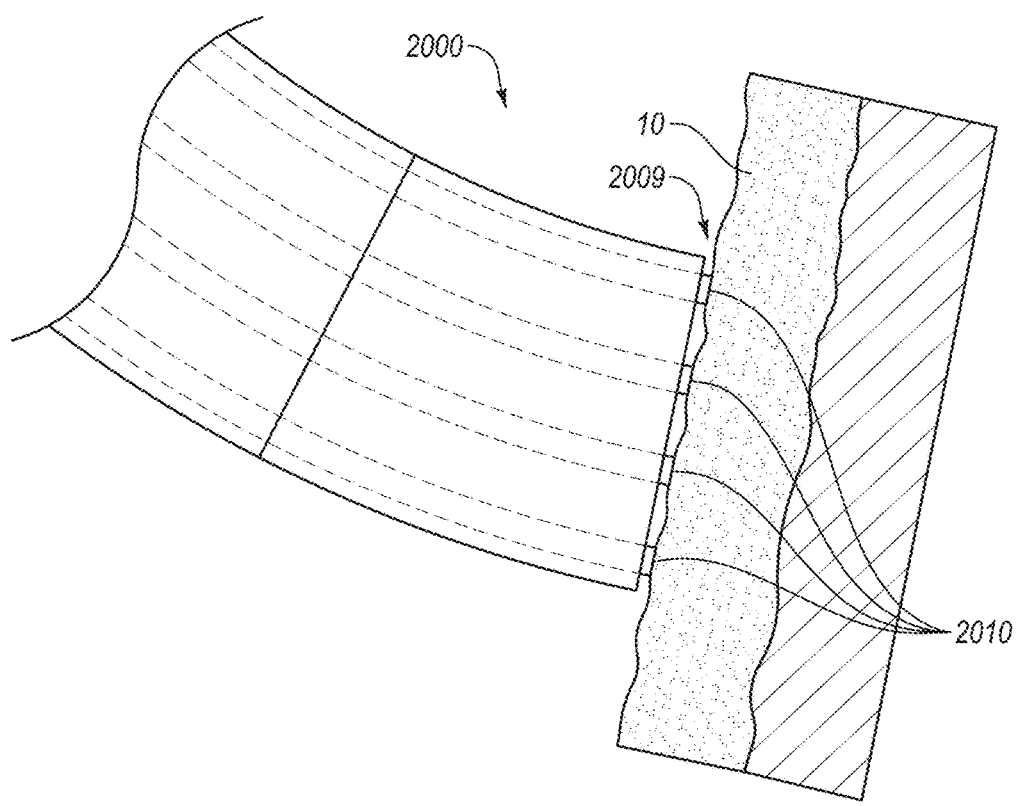
FIG. 20 illustrates an embodiment of a catheter mapping a selected tissue.

FIG. 20 illustrates an embodiment of a catheter 2000 performing a mapping step of a method of treating (e.g., ablating and/or delivering drug) tissue. Components of other devices (e.g., for imaging, treating (e.g., ablating and/or delivering drug), and/or mapping) may be incorporated into, and vice versa, the catheter 2000 of FIG. 20. In the illustrated embodiment, a mapping assembly 2010 may extend beyond a distal tip 2009 of the catheter 2000 so as to come in contact with a selected tissue 10, whether by being selectively advanceable or previously located beyond the distal tip 2009. The mapping assembly may be configured to 2010 record electrical activity within the selected tissue 10.

Figure 21:
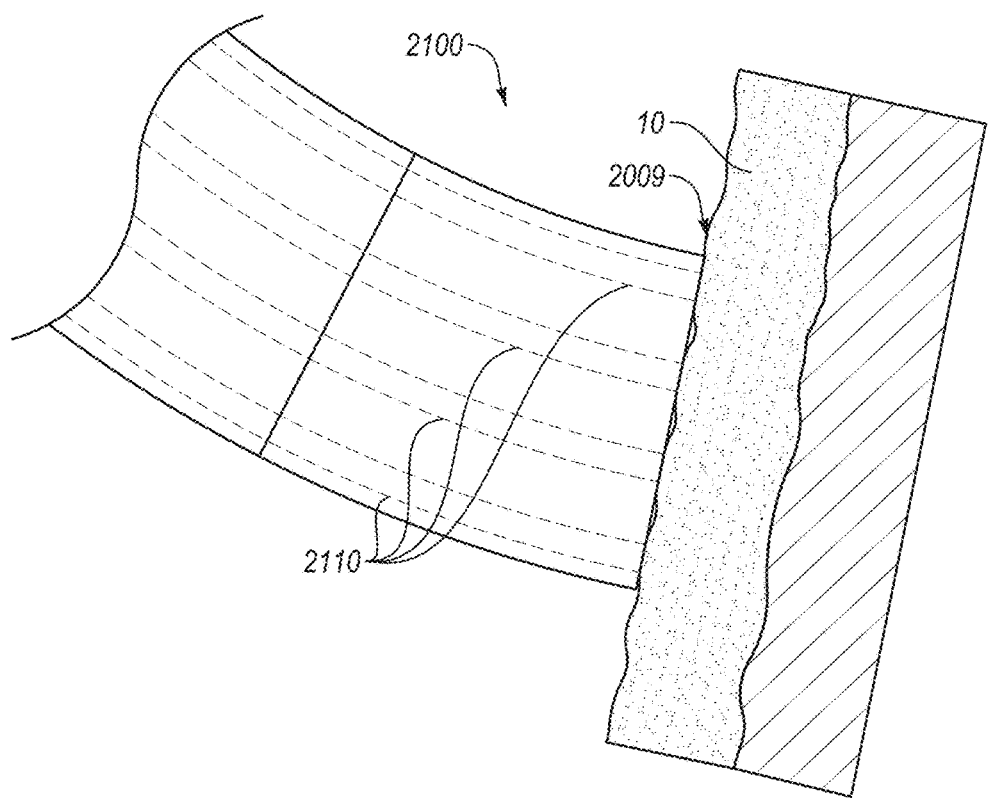
FIG. 21 illustrates another embodiment of a catheter mapping a selected tissue.

FIG. 21 illustrates another embodiment of a catheter 2100 performing a mapping step of a method of treating (e.g., ablating and/or delivering drug) tissue. Components of other devices (e.g., for imaging, treating (e.g., ablating and/or delivering drug), and/or mapping) may be incorporated into, and vice versa, the catheter 2100 of FIG. 21. In the illustrated embodiment, the mapping assembly 2110 has not been extruded beyond a distal tip 2109 of the catheter 2100. The mapping assembly 2110 records electrical activity within the selected tissue 10.

Figure 22:
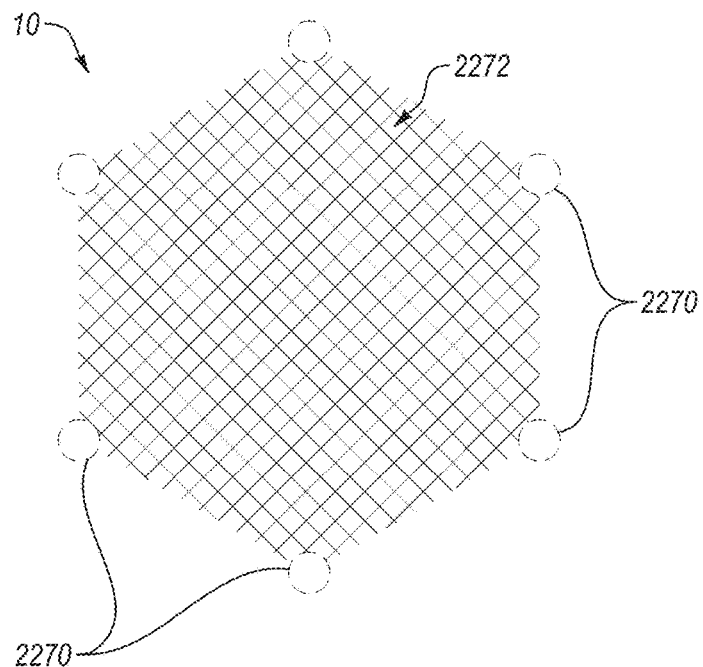
FIG. 22 illustrates a top view of a selected tissue including mapping electrode contact points.

FIG. 22 illustrates a top view of a selected tissue 10 including mapping electrode contact points 2270. A mapped portion 2272 of the selected tissue 10 may reside between the mapping electrode contact points 2270. Electrical information of the mapped portion 2272 of the selected tissue 10 may be measured during the mapping step of the method of treating (e.g., ablating and/or delivering drug) tissue. The mapped portion 2272 may vary based on the location of the mapping electrodes.

Figure 23:
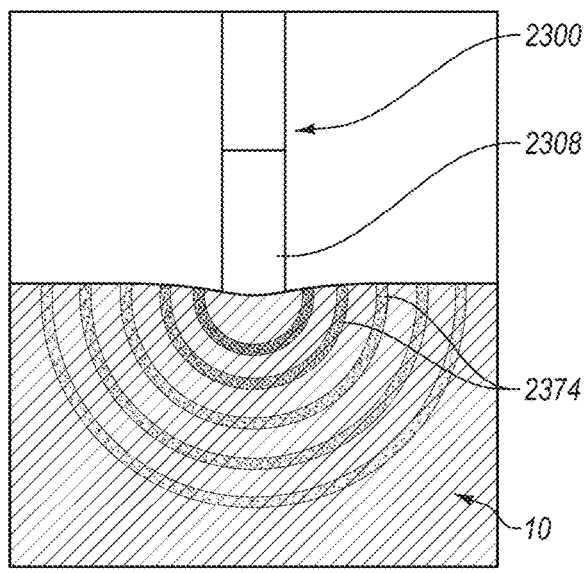
FIG. 23 illustrates an embodiment of a catheter imaging and treating a selected tissue.

FIG. 23 illustrates an embodiment of a catheter 2300 performing a treatment (e.g., ablation and/or drug delivery) step of a method of ablating a selected tissue as described herein with an energy application assembly 2308. RF energy waves 2374 are shown propagating through a depth of a selected tissue 10. The RF energy waves provide energy to the selected tissue 10 in order to increase the temperature of the selected tissue 10 and ablate it. In some embodiments, a drug delivery assembly may be used in addition or in alternative to the energy application assembly 2308.

Figure 24:
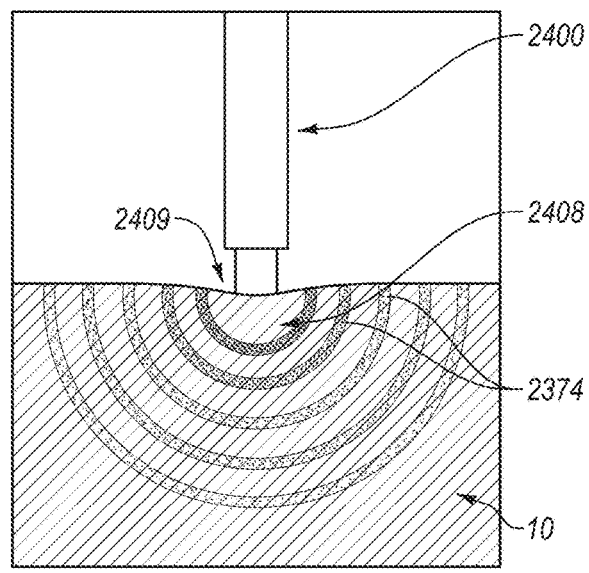
FIG. 24 illustrates another embodiment of a catheter imaging and treating a selected tissue.

FIG. 24 illustrates a similar embodiment as the embodiment illustrated in FIG. 23, but where an energy application assembly has been advanced beyond a distal tip 2409 of a catheter 2400. In this manner, the energy application assembly 2408 may still come into direct contact with a selected tissue 10, even if the catheter 2400 does not. A drug delivery assembly may be similarly advanced in addition or in alternative to the energy application assembly 2408.

Figures 1, 25:
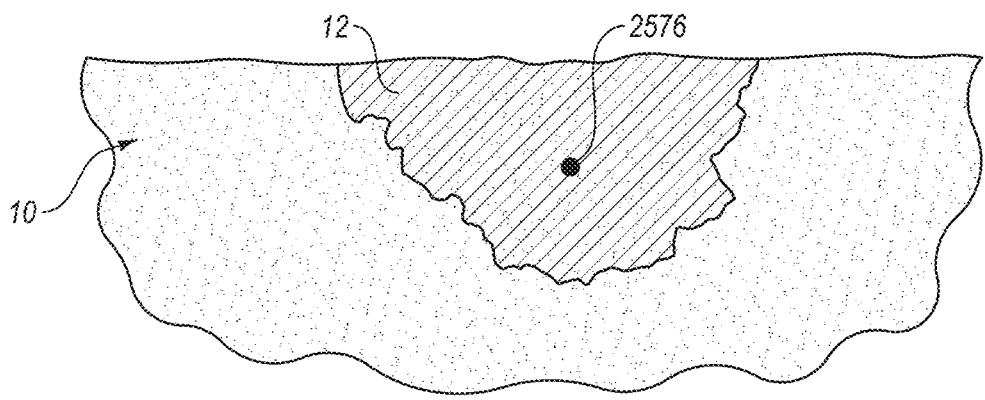
Figures 2, 25:
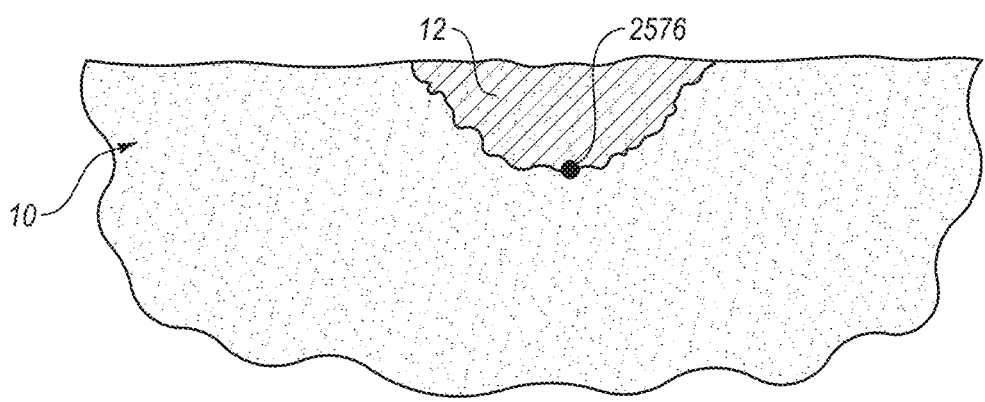
Figures 3, 25:
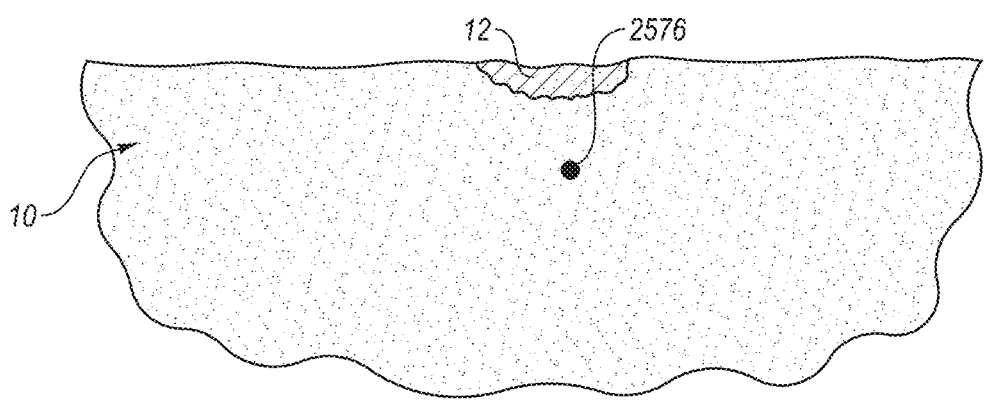

FIGS. 25-1, 25-2, and 25-3 illustrate a cross-sectional view of a tissue 10 that has been ablated. A single ablation step of the method of ablating a selected tissue 10 may or may not ablate the desired tissue. For example, the ablated tissue 12 may extend into a depth of the selected tissue 10 beyond a target 2576. The target 2576 identifies a region within the selected tissue 10 where ablation is desired. As seen in FIGS. 25-2, the ablated tissue 12 may also extend into a depth of the selected tissue 10 up to the target 2576. Also, for example, the ablated tissue 12 may not extend into a depth of the tissue 10 and reach the target 2576. An imaging assembly, such as a confocal microscope imaging assembly herein described, and/or a mapping assembly may provide feedback information to an operator or processor to determine whether sufficient ablation at the target 2576 has occurred. This information may provide outputs to be received by a processor and/or operator. The operator and/or processor may then determine whether or not to re-ablate in the same area and/or the same selected tissue 10, as shown in FIG. 15-2 and described herein, based on the outputs.

Figure 26:
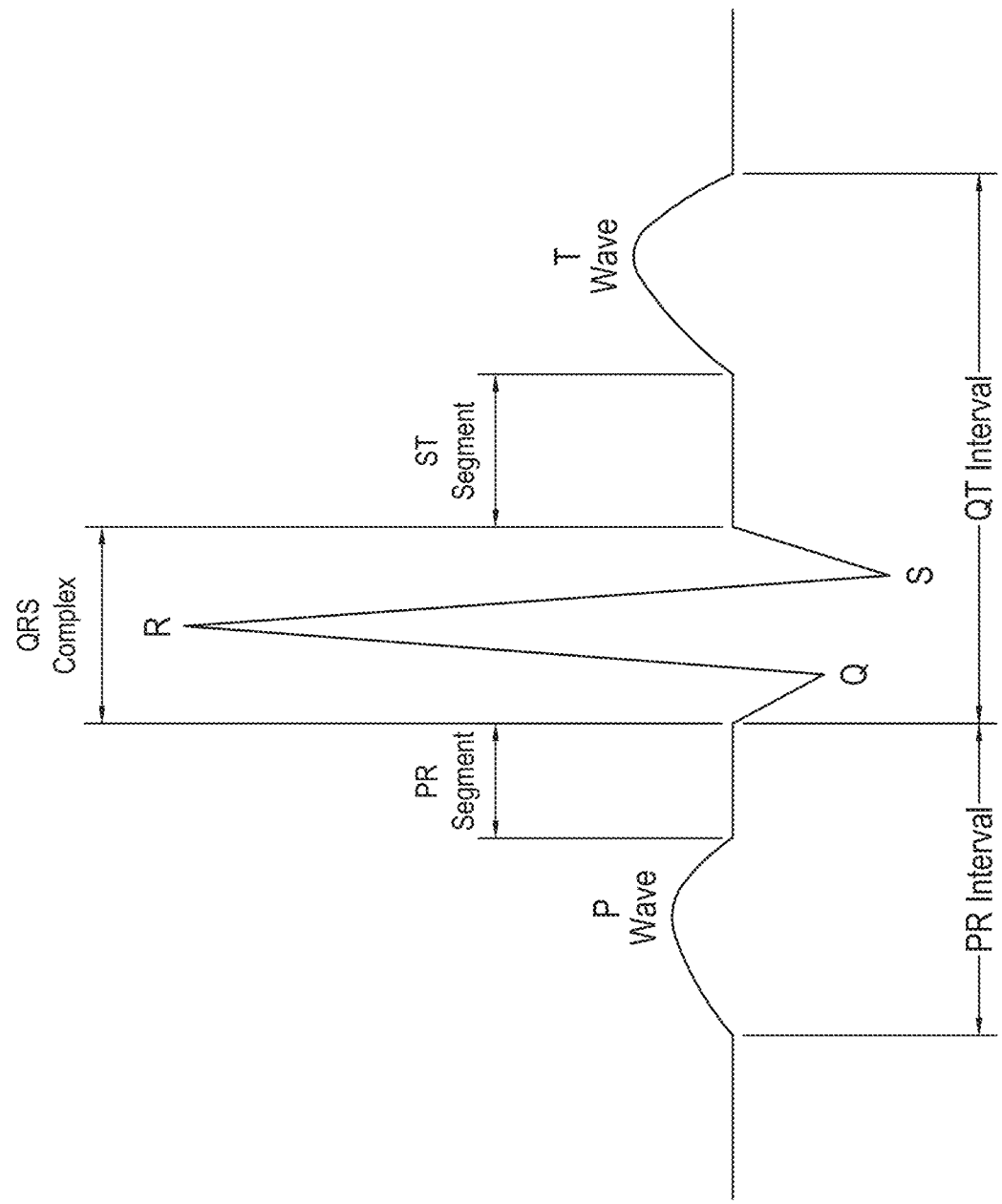
FIG. 26 illustrates an ECG signal of a beating heart.

FIG. 26 illustrates an ECG signal of a beating heart. Certain steps of the method herein described may be timed to take place at a repeatable trace point in time defined by a point on the ECG signal. For example, the trace point may be defined within the ST segment of the ECG signal of a beating heart. Treating (e.g., ablating and/or delivering drug), mapping, and/or imaging steps of the method of treating a selected tissue may be performed only at or near the defined trace point. Other trace points may include different segments of the ECG signal. For example, trace points may be defined within the PR segment or at Q, R, or S, as illustrated in FIG. 26.

Figures 1, 27:
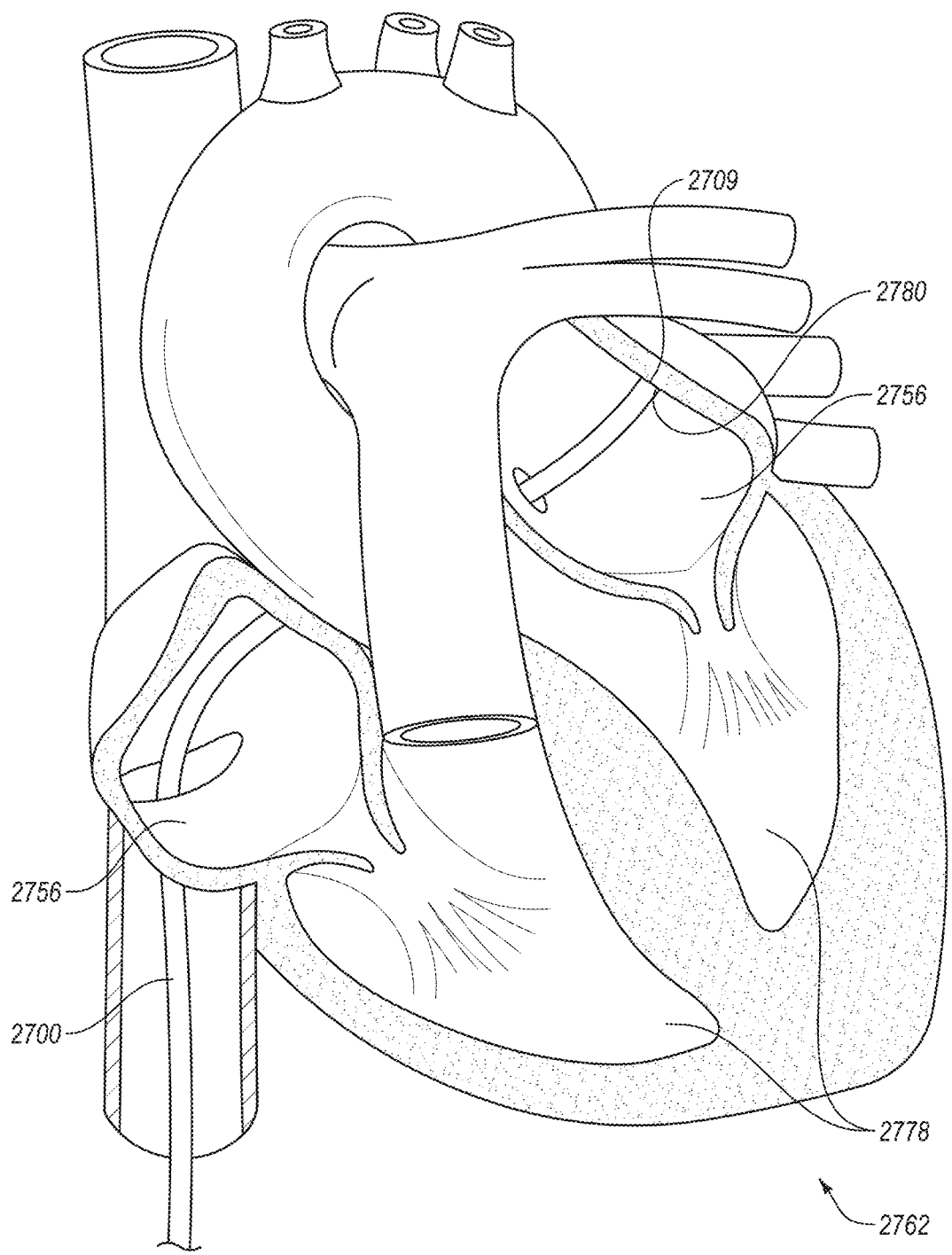
Figures 2, 27:
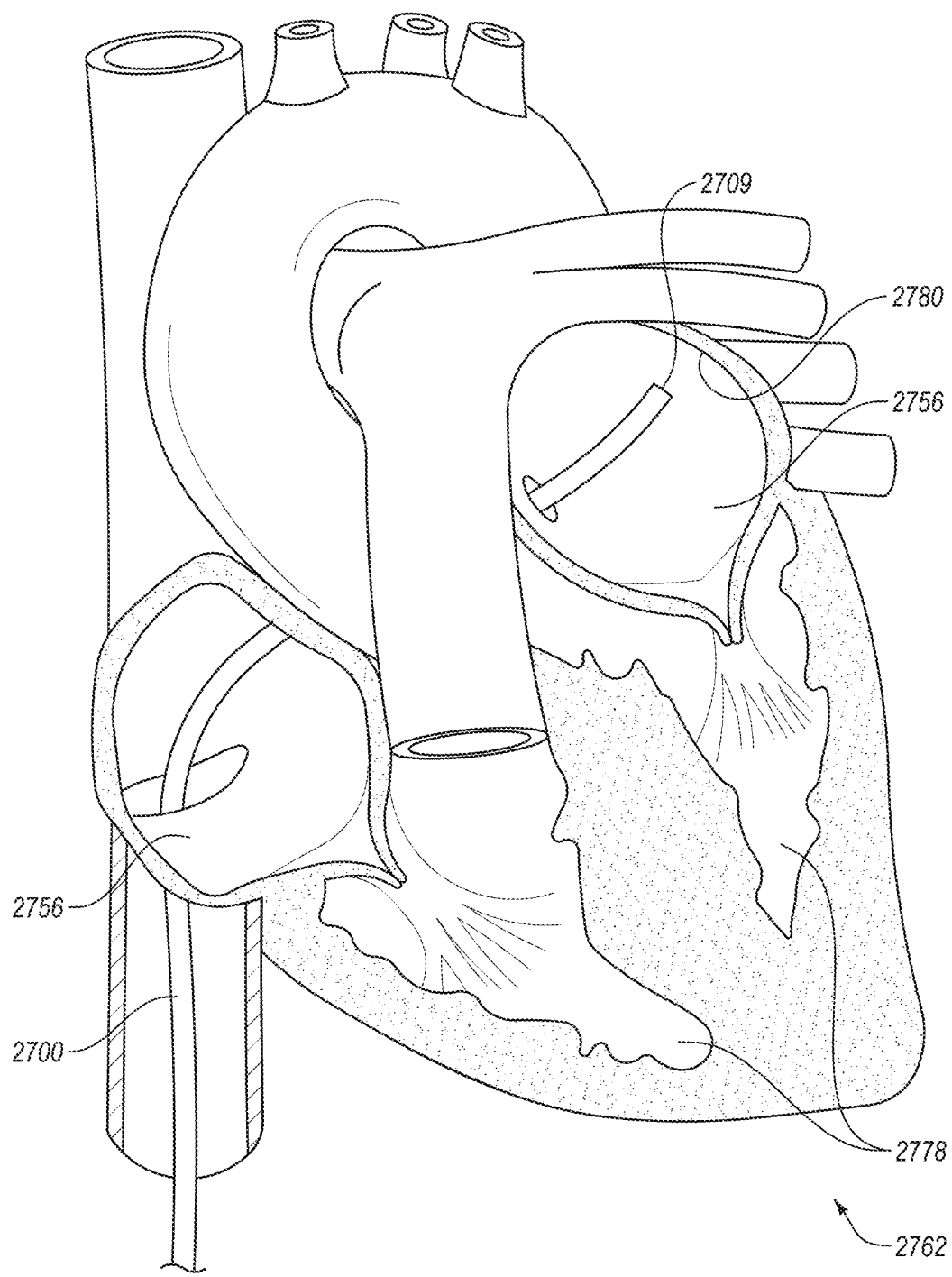

Performing certain steps of the method of treating (e.g., ablating and/or delivering drug) a selected tissue at a repeatable trace point in time may ensure more accurate and repeatable results. As illustrated in FIGS. 27-1 and 27-2, the position of the distal tip 2709 of a catheter 2700 may change relative to tissue within a beating heart during different points along the ECG signal illustrated in FIG. 26. For example, in FIG. 27-1, a catheter 2700 has been inserted into a beating heart 2762. FIG. 27-1 illustrates a heart 2762 where atria 2756 are contracted and the ventricles 2778 are dilated. The contact point 2780 of the catheter 2700 with the selected tissue is shown. As illustrated in FIG. 27-2, the distal tip 2709 of the catheter 2700 is not in contact with the contact point 2780. This is because the heart 2762 is at a different point within the ECG signal where the atria 2756 are dilated and the ventricles 2778 are contracted.

Performing steps of the method of treating (e.g., ablating and/or delivering drug) a selected tissue at a repeatable trace point ensures that treating, mapping, and imaging steps of the method are done while the catheter 2700 is in the same position relative to the selected tissue contact point 2780. This may ensure more repeatable and reliable treatment results.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references (e.g., journal articles, published patent applications, patents, websites, and the like) that are recited herein are incorporated herein by specific reference in their entirety.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value. For example, the use of the term "parallel" may include deviations from parallel of within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims. It should be understood that any directions or reference frames in the preceding description are merely relative directions or movements. For example, any references to "front" and "back" or "top" and "bottom" or "left" and "right" are merely descriptive of the relative position or movement of the related elements.

What is claimed is:

1. A device for imaging and treating targeted cardiac tissue of a subject, the device comprising:
    an elongated sheath extending between a distal end and a proximal end, the elongated sheath having a lumen;
    a housing of fixed size disposed at the distal end of the elongated sheath and forming a distal tip of the device, the housing having a distally-facing aperture and comprising a conductive material;
    a fiber-optic bundle extending through the lumen of the sheath to the aperture and being in communication with the aperture, the fiber-optic bundle being disposed so as to transmit and receive light through the aperture;
    one or more energy application wires extending through the lumen of the sheath and conductively coupling with the housing to enable transfer of energy through the one or more energy application wires to the housing; and
    one or more mapping electrodes disposed as rings around the circumference of the sheath and/or housing, wherein the rings are spaced apart and disposed at different axial locations along a length of the sheath and/or housing.

2. The device of claim 1, wherein the energy application wires and the housing are configured to transfer one or more of radiofrequency electrical waves, microwaves, heat, and cold.

3. The device of claim 1, wherein the housing includes an inner section and an outer section, the inner section being formed of an insulating material and the outer section comprising the conductive.

4. The device of claim 3, wherein one or more lenses are housed within the inner section, the one or more lenses being in communication with the fiber-optic bundle.

5. The device of claim 3, wherein the outer section circumferentially surrounds the inner section, and the inner section defines the aperture.

6. The device of claim 1, wherein an exterior circumference of the housing is conductive.

7. The device of claim 1, wherein the elongated sheath is steerable.

8. The device of claim 1, wherein the fiber-optic bundle is configured to produce an image of tissue of the subject at a resolution of less than about 4 µm.

9. A device for imaging and treating targeted cardiac tissue of a subject, the device comprising:
    an elongated sheath extending between a distal end and a proximal end, the elongated sheath having a lumen;
    a housing of fixed size and shape disposed at the distal end of the elongated sheath and forming a distal tip of the device, the housing having a distally-facing aperture and being formed at least partially of a conductive material;
    a fiber-optic bundle extending through the lumen of the sheath to the housing and being in communication with one or more lenses disposed within the housing and with the aperture, the fiber-optic bundle being disposed so as to transmit and receive light through the aperture;
    one or more energy application wires extending through the lumen of the sheath and conductively coupling with the housing to enable transfer of energy through the one or more energy application wires to the housing; and
    one or more mapping electrodes disposed as rings around the circumference of the sheath and/or housing, wherein the rings are spaced apart and disposed at different axial locations along a length of the sheath and/or housing.

10. The device of claim 9, wherein the housing includes an inner section and an outer section, the inner section being formed of an insulating material and the outer section comprising the conductive material.

11. The device of claim 10, wherein the outer section circumferentially surrounds the inner section, and the inner section defines the aperture.

12. The device of claim 9, wherein the energy application wires and the housing are configured to transfer one or more of radiofrequency electrical waves, microwaves, heat, or cold.

13. The device of claim 9, wherein the elongated sheath is steerable.

14. A device for imaging and treating targeted cardiac tissue of a subject, the device comprising:
    an elongated sheath extending between a distal end and a proximal end, the elongated sheath having a lumen;
    a housing of fixed size disposed at the distal end of the elongated sheath and forming a distal tip of the device, the housing having a distally-facing aperture and comprising a conductive material;
    a confocal microscope assembly comprising a fiber-optic bundle extending through the lumen of the sheath to the aperture and being in communication with the aperture, the fiber-optic bundle being disposed so as to transmit and receive light through the aperture;

one or more energy application wires extending through the lumen of the sheath and conductively coupling with the housing to enable transfer of energy through the one or more energy application wires to the housing; and one or more mapping electrodes disposed as rings around the circumference of the sheath and/or housing, wherein the rings are spaced apart and disposed at different axial locations along a length of the sheath and/or housing.

15. The device of claim 14, wherein the elongated sheath is steerable.

16. The device of claim 14, wherein the fiber-optic bundle is configured to produce an image of tissue of the subject at a resolution of less than about 4 μm.

17. The device of claim 14, wherein the housing includes an inner section formed from an insulating material and an outer section formed from the conductive material, the outer section circumferentially surrounding the inner section.

18. The device of claim 17, wherein the outer section circumferentially surrounds the inner section, and the inner section defines the aperture.

19. The device of claim 17, wherein one or more lenses are housed within the inner section, the one or more lenses being in communication with the fiber-optic bundle.

20. The device of claim 14, wherein the energy application wires and the housing are configured to transfer one or more of radiofrequency electrical waves, microwaves, heat, or cold.

* * * * *